(12) United States Patent
Ding et al.

(10) Patent No.: US 7,176,312 B2
(45) Date of Patent: Feb. 13, 2007

(54) KINASE INHIBITOR SCAFFOLDS AND METHODS FOR THEIR PREPARATION

(75) Inventors: Sheng Ding, San Diego, CA (US); Qiang Ding, San Diego, CA (US); Nathanael S. Gray, San Diego, CA (US)

(73) Assignees: The Scripps Research Institute, La Jolla, CA (US); IRM LLC (BM)

( * ) Notice: Subject to any disclaimer, the term of this patent is extended or adjusted under 35 U.S.C. 154(b) by 0 days.

(21) Appl. No.: 10/270,030

(22) Filed: Oct. 12, 2002

(65) Prior Publication Data

US 2003/0191312 A1 Oct. 9, 2003

Related U.S. Application Data

(60) Provisional application No. 60/348,089, filed on Jan. 10, 2002, provisional application No. 60/346,480, filed on Jan. 7, 2002, provisional application No. 60/331,835, filed on Nov. 20, 2001, provisional application No. 60/328,763, filed on Oct. 12, 2001.

(51) Int. Cl.
- *C07D 473/16* (2006.01)
- *C07D 487/04* (2006.01)
- *C07D 239/94* (2006.01)
- *C07D 401/14* (2006.01)
- *C07D 403/12* (2006.01)

(52) U.S. Cl. ...... 544/277; 544/264; 544/276; 544/265; 544/224; 544/237; 544/239; 544/336; 544/408; 544/316; 544/320; 544/322; 544/323; 544/326; 544/330; 544/286; 544/287; 544/291; 544/292; 544/293; 544/353; 544/354; 546/304; 546/307; 546/312; 546/153; 546/159; 546/160; 546/171; 435/4; 548/557; 548/558; 548/559; 548/469; 548/483; 548/484; 548/306.4; 548/307.4; 548/307.7; 548/308.1

(58) Field of Classification Search ............... None
See application file for complete search history.

(56) References Cited

U.S. PATENT DOCUMENTS

2003/0171583 A1* 9/2003 Ding et al. .................. 544/277
2004/0157864 A1* 8/2004 Wu et al. .................... 544/276

FOREIGN PATENT DOCUMENTS

WO  WO 99/34018 A1  8/1999

OTHER PUBLICATIONS

Ying Zhao and Anne M. Baranger J. Am. Chem. Soc.;2003; 125(9) pp. 2480-2488.*
Scholl et al., Tetrahedron Lett., 40, 2247 (1999).*
Scholl et al., Org. Lett., 1, 953 (1999).*
Bellina Synthesis #15, 2419 (2004).*
Strem Chemical incorporated, Catalog item #07-0299.*
Zhang J. Org. Chem 64(11) 3804 (1999).*
Dubbaka et al., Organic Letters 6, 95 (2004).*
Hermann, Angewante Chem. Int. Ed. 41. 1290-1309 (2002).*
Strem Chemicals, Inc. Catalog # 07-0302.*
Zhao et al., "Design of an adenosine Analogue that Selectively Improves the Affinity of a Mutant U1AProtein for RNA," *J. Am. Chem. Soc.*, 125:2480-2488 (2003).
Ding et al., "A Concise and Traceless Linker Strategy toward Combinatorial Libraries of 2,6,9-Substituted Purines," *J. Org. Chem.*, 66:8273-8276 (2001).
Ding et al., "Expanding the diversity of purine libraries," *Tetrahedron Letters*, 42:8571-8755 (2001).

* cited by examiner

*Primary Examiner*—Mark L. Berch
(74) *Attorney, Agent, or Firm*—Townsend & Townsend & Crew LLP

(57) ABSTRACT

General methods for the solution phase as well as solid phase synthesis of various substituted heteroaryls has been demonstrated. These substituted heteroaryls can be further elaborated by aromatic substitution with amines at elevated temperature or by anilines, boronic acids and phenols via palladium catalyzed cross-coupling reactions.

20 Claims, 2 Drawing Sheets

KINASE INHIBITOR SCAFFOLDS AND METHODS FOR THEIR PREPARATION

CROSS-REFERENCES TO RELATED APPLICATIONS

This patent application claims the benefit of U.S. Provisional Patent Application No. 60/328,763, filed Oct. 12, 2001, U.S. Provisional Patent Application No. 60/331,835, filed Nov. 20, 2001, U.S. Provisional Patent Application No. 60/346,480, filed Jan. 7, 2002 and U.S. Provisional Patent Application No. 60/348,089, filed Jan. 10, 2002, the teachings of all of which are incorporated herein by reference. This patent application is related to U.S. Provisional Patent Application No. 60/328,741, filed Oct. 12, 2001, U.S. Provisional Patent Application No. 60/346,552, filed Jan. 7, 2002, U.S. Provisional Patent Application No. 60/347,037, filed Jan. 8, 2002, the teachings of all of which are incorporated herein by reference.

BACKGROUND OF THE INVENTION

With the large number of novel proteins being derived from genomics, proteomics, and traditional biochemical approaches there is a tremendous need to develop more efficient methods for the discovery and optimization of small molecule ligands to help determine the biological function of these proteins. Not surprisingly, many of these new targets come from protein families that have received considerable attention ((a) Dolle, R. E., *Molecular Diversity*, 3, 199 (1998); (b) Dolle et al., *J. Comb. Chem.*, 1, 235 (1999); (c) Dolle, R. E., *J. Comb. Chem.*, 2, 383 (2000) and references therein) in the past such as GPCRs, proteases, and kinases. This presents the combinatorial chemists with the opportunity to take scaffolds developed against a particular protein family member and develop generalized synthetic schemes that allow other family members to be selectively targeted.

A survey of the literature (McMahon et al., *Current Opinion in Drug Discovery & Development*, 1, 131 (1998); Adams et al., *Current Opinion in Drug Discovery & Development*, 2, 96 (1999); Garcia-Echeverria et al., *Med. Res. Rev*, 20, 28 (2000) and references therein) reveals that the vast majority of kinase inhibitor scaffolds consist of planar heteroaryls that present both key hydrogen bond donating/ accepting functionality and proper hydrophobicity (FIG. 1).

The purine ring is a prime example of one of these planar heteroaryls. Guanosine and adenosine, two of the most common purines, serve as key recognition and anchoring elements in a variety of cofactors and signaling molecules (e.g., ATP, GTP, cAMP, cGMP, adoMet, adenosine and NADH). Correspondingly, an enormous number of proteins have evolved to recognize the purine motif including reductases, polymerases, G-proteins, methyltransferases, and protein kinases. Despite the abundance of protein kinases (Venter, J. C. et al., *Science*, 291, 1304 (2001)) (estimated to be encoded by 2 to 5% of the eukaryotic genome) and the high degree of conservation of active site residues, ATP-binding site directed inhibitors have been designed that are highly specific. For example, ST1571 (Druker et al., *Nat. Med.*, 2, 561 (1996); Zimmermann et al., *Bioorg. Med. Chem. Lett.*, 7, 187 (1997); Schindler et al., *Science*, 289, 1938 (2000)) has been developed as a potent and selective Ab1 kinase inhibitor, and is in use for the treatment of chronic myelogenous leukemia (CML). Screens of purine libraries (Gray et al., *Science*, 281, 533 (1998) and references therein; Rosania et al., *Proc. Natl. Acad. Sci. USA*, 96, 4797 (1999); Chang et al., *Chemistry and Biology*, 6, 361 (1999)) have resulted in the identification of diverse purines that inhibit mitosis, alter cellular morphology, and induce apoptosis. By constructing new purine derivatives, we hope to develop inhibitors of different ATP-dependent proteins, which will be useful for elucidating function and potentially provide starting points for the development of new therapeutics.

Previous syntheses of purine libraries have relied on nucleophilic-aromatic substitution and alkylation chemistry to derivatize the 2-, 6- and 9-positions of the purine ring. One of the primary limitations of this chemistry is the inability to access a large number of pharmacologically relevant derivatives bearing aryl, anilino or phenolic substituents. In addition, the sluggish aromatic substitution of 2-fluoro or 2-chloro substituted purine compounds precludes the introduction of sterically hindered amines or anilines (Chang et al., *Chemistry and Biology*, 6, 361 (1999)).

Recently, there have been significant advances in methodology for performing palladium-catalyzed C—C, C—N and C—O bond formation reactions with a wide variety of substrates. For example, new phosphine ligands (Wolfe et al., *J. Am. Chem. Soc.*, 121, 9550 (1999); Stürmer, R., *Angew. Chem. Int. Ed.*, 38, 3307 (1999) and references therein; Wolfe et al., *J. Org. Chem.*, 65, 1158 (2000)) have allowed palladium mediated functionalization of inexpensive chloroarenes with boronic acids and amines at room temperature. 1,3-Dimesityl-imidazolin-2-ylidene and its saturated analog, originally developed by Grubbs as carbene ligands for ruthenium-based olefin metathesis catalysts (Scholl et al., *Tetrahedron Lett.*, 40, 2247 (1999); Scholl et al., *Org. Lett.*, 1, 953 12 (1999)), have also been found to be highly effective ligands.

In view of the above, a method using transition metal-catalyzed coupling reaction for the preparation of substituted purines, as well as other planar heteroaryls, would provide access to a greater diversity of substituted planar heteroaryls. Application of this method for the preparation of libraries of planar heteroaryls, which is based on a combinatorial scaffold approach, would represent a significant advance in the art. Surprisingly, the present invention provides such a method and compounds produced by the method.

BRIEF SUMMARY OF THE INVENTION

The present invention provides, inter alia, methods for the preparation of heteroaryls using both solution phase and solid phase chemistry. The methods of the present invention are useful for the preparation of a wide array of kinase inhibitor scaffolds and kinase inhibitors. Both the solution and solid phase synthesis methodologies of the present method provides scaffolds and inhibitors, which are synthesized rapidly and which are substantially free of side products. In particular, the methods of the present invention are useful for preparing kinase-directed heteroaryl libraries using a combinatorial scaffold approach.

In addition to the method for preparing kinase inhibitor scaffolds and kinase inhibitors and, in particular, combinatorial libraries of such kinase inhibitors, the present invention provides kinase inhibitor scaffolds and kinase inhibitors and, in particular, arrays or libraries of kinase inhibitors that are based on diverse planar heteroarylalkyl and heteroaryl core molecules having pendant substituents. Representative core molecules include, but are not limited to, both substituted and unsubstituted purines, pyrimidines, quinazolines, pyrazines, pyridazines, quinoxalines, phthalazines and thiadiazoles. Other appropriate planar heteroaryl scaffold components will be both apparent, and readily accessible to those of skill in the art.

The scaffolds and inhibitors of the invention are prepared by an unexpectedly efficient process for adding elements of diversity to a scaffold element using solution phase as well as solid phase synthetic methodologies.

Other objects and advantages of the present invention will be apparent from the detailed description and examples that follow.

DETAILED DESCRIPTION OF THE INVENTION AND PREFERRED EMBODIMENTS

Definitions

Figure 1:
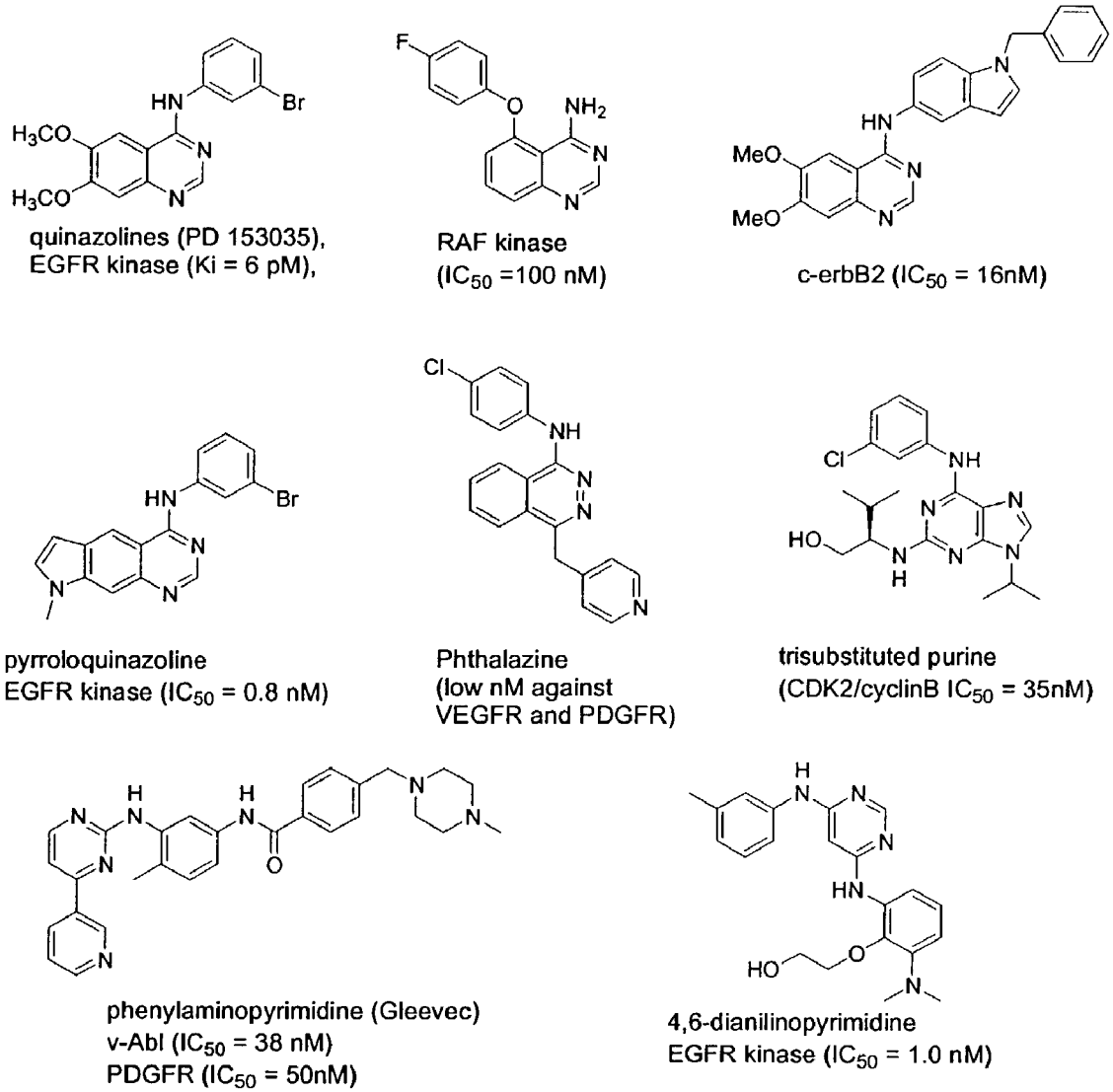
FIG. 1 displays diverse kinase inhibitor scaffolds.
Figure 2:
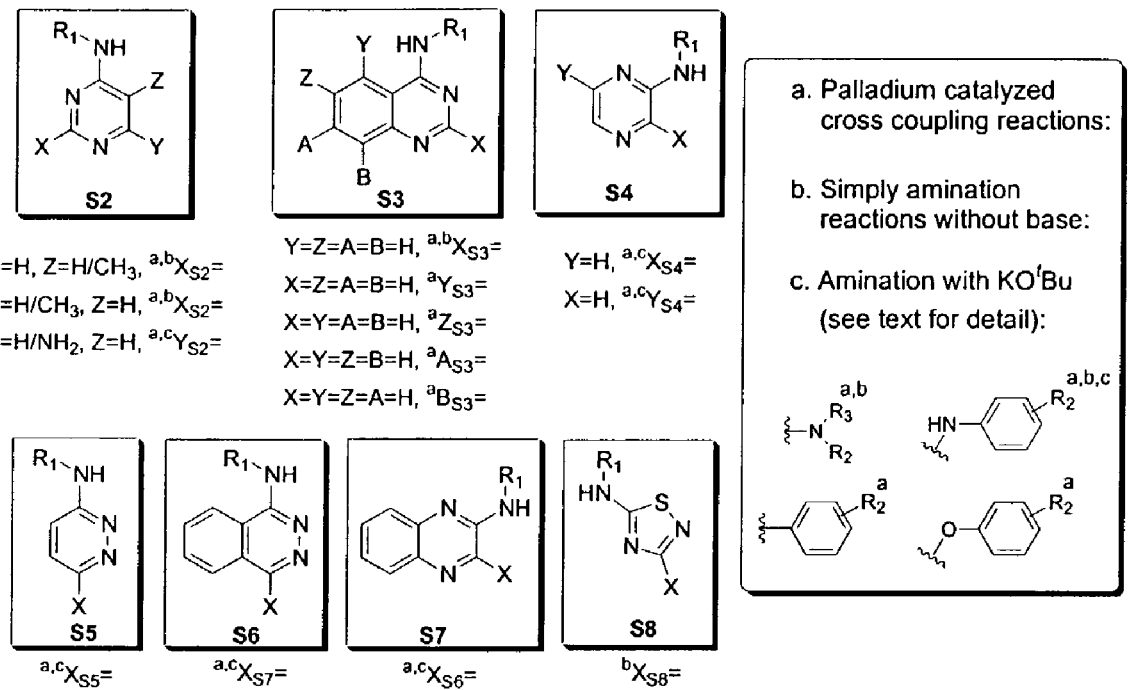
FIG. 2 displays examples of diverse heteroaryls constructed by combinatorial scaffold approach of the invention.

Unless defined otherwise, all technical and scientific terms used herein generally have the same meaning as commonly understood by one of ordinary skill in the art to which this invention belongs. Generally, the nomenclature used herein and the laboratory procedures for organic and analytical chemistry are those well known and commonly employed in the art.

As used herein, the term "leaving group" refers to a portion of a substrate that is cleaved from the substrate in a reaction.

"Protecting group," as used herein refers to a portion of a substrate that is substantially stable under a particular reaction condition, but which is cleaved from the substrate under a different reaction condition. A protecting group can also be selected such that it participates in the direct oxidation of the aromatic ring component of the compounds of the invention. For examples of useful protecting groups, see, for example, Greene et al., *Protective Groups in Organic Synthesis*, John Wiley & Sons, New York (1991).

The term "alkyl," by itself or as part of another substituent, means, unless otherwise stated, a straight or branched chain hydrocarbon radical, having the number of carbon atoms designated (i.e. $C_1$–$C_{10}$ means one to ten carbons). Examples of saturated hydrocarbon radicals include groups such as methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl, and the like.

The terms "alkenyl" and "alkynyl" refer to unsaturated hydrocarbon groups having one or more double bonds or triple bonds, respectively. Examples of suitable unsaturated hydrocarbon groups include vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. The term "cycloalkyl" refers to a cyclic hydrocarbon radical, having the number of carbon atoms designated (i.e. $C_1$–$C_{10}$ means one to ten carbons). Examples of suitable cycloalkyls include cyclohexyl, (cyclohexyl)methyl, cyclopropylmethyl and the like.

The terms "alkoxy," "alkylamino" and "alkylthio" (or thioalkoxy) are used in their conventional sense, and refer to those alkyl groups attached to the remainder of the molecule via an oxygen atom, an amino group, or a sulfur atom, respectively.

The term "heteroalkyl," by itself or in combination with another term, means, unless otherwise stated, a stable straight or branched chain, or cyclic hydrocarbon radical, or combinations thereof, consisting of the stated number of carbon atoms and from one to three heteroatoms selected from the group consisting of O, N, Si and S, and wherein the nitrogen and sulfur atoms may optionally be oxidized and the nitrogen heteroatom may optionally be quaternized. The heteroatom(s) O, N and S may be placed at any interior position of the heteroalkyl group. The heteroatom Si may be placed at any position of the heteroalkyl group, including the position at which the alkyl group is attached to the remainder of the molecule. Examples include —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$,—S(O)—$CH_3$, —$CH_2$—$CH_2$—S(O)$_2$—$CH_3$, —CH=CH—O—$CH_3$, —Si($CH_3$)$_3$, —$CH_2$—CH=N—O$CH_3$, and —CH=CH—N($CH_3$)—$CH_3$. Up to two heteroatoms may be consecutive, such as, for example, —$CH_2$—NH—O$CH_3$ and —$CH_2$—O—Si($CH_3$)$_3$. Similarly, the term "heteroalkylene" by itself or as part of another substituent means a divalent radical derived from heteroalkyl, as exemplified by —$CH_2$—$CH_2$—S—$CH_2$$CH_2$— and —$CH_2$—S—$CH_2$—$CH_2$—NH—$CH_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied.

The terms "cycloalkyl" and "heterocycloalkyl", by themselves or in combination with other terms, represent, unless otherwise stated, cyclic versions of "alkyl" and "heteroalkyl", respectively. Additionally, for heterocycloalkyl, a heteroatom can occupy the position at which the heterocycle is attached to the remainder of the molecule. Examples of cycloalkyl include cyclopentyl, cyclohexyl, 1-cyclohexenyl, 3-cyclohexenyl, cycloheptyl, and the like. Examples of heterocycloalkyl include 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like.

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "halo($C_1$–$C_4$)alkyl" is mean to include trifluoromethyl, 2,2,2-trifluoroethyl, 4-chlorobutyl, 3-bromopropyl, and the like. In the specific embodiments described herein, a particular halogen (e.g., chloro) is sometimes specified. However, one of skill in the art could substitute a different halogen for the one exemplified.

The term "aryl" means, unless otherwise stated an aromatic, hydrocarbon substituent, which can be a single ring or multiple rings (up to three rings), which are fused together or linked covalently. The term "heteroaryl" refers to aryl groups (or rings) that contain from zero to four heteroatoms selected from N, O, and S, wherein the nitrogen and sulfur atoms are optionally oxidized, and the nitrogen atom(s) are optionally quaternized. A heteroaryl group can be attached to the remainder of the molecule through a heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below.

For brevity, the term "aryl" when used in combination with other terms (e.g., aryloxy, arylthioxy, arylalkyl) includes both aryl and heteroaryl rings as defined above. Thus, the term "arylalkyl" is meant to include those radicals in which an aryl group is attached to an alkyl group (e.g., benzyl, phenethyl, pyridylmethyl and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like).

Each of the above terms (e.g., "alkyl," "heteroalkyl," "aryl" and "heteroaryl") are meant to include both substituted and unsubstituted forms of the indicated radical. Preferred substituents for each type of radical are provided below.

Each of the above terms (e.g., "alkyl," "heteroalkyl," "aryl" and "heteroaryl") is meant to include both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to: —OR', =O, =NR', =N—OR', —NR'R", —SR', -halogen, —SiR'R"R''', —OC(O)R', —C(O)R', —CO$_2$R', —CONR'R", —OC(O)NR'R", —NR"C(O)R', —NR'—C(O)NR"R''', —NR"C(O)$_2$R', —NR—C(NR'R"R''')=NR'''', —NR—C(NR'R")=NR''', —S(O)R', —S(O)$_2$R', —S(O)$_2$NR'R", —NRSO$_2$R', —CN and —NO$_2$ in a number ranging from zero to (2m'+1), where m' is the total number of carbon atoms in such radical. R', R", R''' and R'''' each preferably independently refer to hydrogen, substituted or unsubstituted heteroalkyl, substituted or unsubstituted aryl, e.g., aryl substituted with 1–3 halogens, substituted or unsubstituted alkyl, alkoxy or thioalkoxy groups, or arylalkyl groups. When a compound of the invention includes more than one R group, for example, each of the R groups is independently selected as are each R', R", R''' and R'''' groups when more than one of these groups is present. When R' and R" are attached to the same nitrogen atom, they can be combined with the nitrogen atom to form a 5-, 6-, or 7-membered ring. For example, —NR'R" is meant to include, but not be limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

Similar to the substituents described for the alkyl radical, substituents for the aryl and heteroaryl groups are varied and are selected from, for example: halogen, —OR', =O, =NR', =N—OR', —NR'R", —SR', -halogen, —SiR'R"R''', —OC(O)R', —C(O)R', —CO$_2$R', —CONR'R", —OC(O)NR'R", —NR"C(O)R', —NR'—C(O)NR"R''', —NR"C(O)$_2$R', —NR—C(NR'R")=NR''', —S(O)R', —S(O)$_2$R', —S(O)$_2$ NR'R", —NRSO$_2$R', —CN and —NO$_2$, —R', —N$_3$, —CH(Ph)$_2$, fluoro(C$_1$–C$_4$)alkoxy, and fluoro(C$_1$–C$_4$)alkyl, in a number ranging from zero to the total number of open valences on the aromatic ring system; and where R', R", R''' and R'''' are preferably independently selected from hydrogen, (C$_1$–C$_8$)alkyl and heteroalkyl, unsubstituted aryl and heteroaryl, (unsubstituted aryl)-(C$_1$–C$_4$)alkyl, and (unsubstituted aryl)oxy-(C$_1$–C$_4$)alkyl. When a compound of the invention includes more than one R group, for example, each of the R groups is independently selected as are each R', R", R''' and R'''' groups when more than one of these groups is present.

Two of the substituents on adjacent atoms of the aryl or heteroaryl ring may optionally be replaced with a substituent of the formula —T—C(O)—(CRR')$_q$—U—, wherein T and U are independently —NR—, —O—, —CRR'— or a single bond, and q is an integer of from 0 to 3. Alternatively, two of the substituents on adjacent atoms of the aryl or heteroaryl ring may optionally be replaced with a substituent of the formula —A—(CH$_2$)$_r$—B—, wherein A and B are independently —CRR'—, —O—, —NR—, —S—, —S(O)—, —S(O)$_2$—, —S(O)$_2$NR'— or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X—(CR"R''')$_d$—, where s and d are independently integers of from 0 to 3, and X is —O—, —NR'—, —S—, —S(O)—, —S(O)$_2$—, or —S(O)$_2$NR'—. The substituents R, R', R" and R''' are preferably independently selected from hydrogen or substituted or unsubstituted (C$_1$–C$_6$)alkyl.

As used herein, the term "heterocycle," refers to both heterocycloalkyl and heteroaryl groups.

As used herein, the term "heteroatom" is meant to include oxygen (O), nitrogen (N), sulfur (S) and silicon (Si).

The term "pharmaceutically acceptable salts" is meant to include salts of the active compounds which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge et al., *Journal of Pharmaceutical Science*, 66, 1–19 (1977)). Certain specific compounds of the present invention contain both basic and acidic functionalities that allow the compounds to be converted into either base or acid addition salts.

The neutral forms of the compounds are preferably regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

In addition to salt forms, the present invention provides compounds, which are in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

Certain compounds of the present invention can exist in unsolvated forms as well as solvated forms, including hydrated forms. In general, the solvated forms are equivalent to unsolvated forms and are intended to be encompassed within the scope of the present invention. Certain compounds of the present invention may exist in multiple crystalline or amorphous forms. In general, all physical forms are equivalent for the uses contemplated by the present invention and are intended to be within the scope of the present invention.

Certain compounds of the present invention possess asymmetric carbon atoms (optical centers) or double bonds; the racemates, diastereomers, geometric isomers and individual isomers are encompassed within the scope of the present invention.

The compounds of the present invention may also contain unnatural proportions of atomic isotopes at one or more of the atoms that constitute such compounds. For example, the compounds may be radiolabeled with radioactive isotopes, such as for example tritium ($^3H$), iodine-125 ($^{125}I$) or carbon-14 ($^{14}C$). All isotopic variations of the compounds of the present invention, whether radioactive or not, are intended to be encompassed within the scope of the present invention.

The Compounds

In a first aspect, the present invention provides a compound having a structure selected from the following:

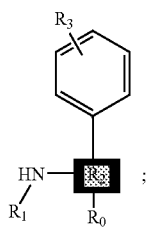 ; 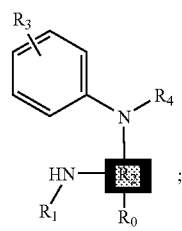 ;

-continued

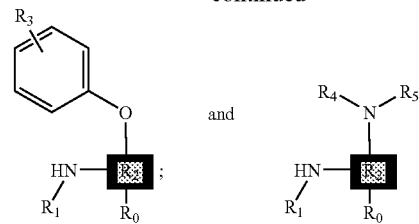

In the Formulae displayed immediately above, $R_0$ is a functional group including, but not limited to, substituted or unsubstituted alkyl, substituted or unsubstituted heteroalkyl and acyl groups. $R_1$ is a functional group including, but not limited to, substituted or unsubstituted alkyl and substituted or unsubstituted heteroalkyl. $R_2$ is a functional group including, but not limited to, substituted or unsubstituted planar heterocyclic or heteroaryl moiety. $R_3$, $R_4$ and $R_5$ are independently selected and are functional groups including, but not limited to, substituted or unsubstituted alkyl, substituted or unsubstituted heteroalkyl, substituted or unsubstituted aryl, substituted or unsubstituted heteroaryl, substituted or unsubstituted heterocycloalkyl, halogens, and alkoxy groups.

In one embodiment, the present invention provides a compound having the following formula:

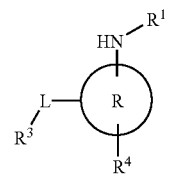

XV

In Formula XV, R is a functional group including, but not limited to, a 5- or 6-membered heteroaryl and a 9- or 10-membered 6,5- or 6,6-fused heteroaryl, containing from 1–4 nitrogen atoms, optionally substituted with 1–2 functional groups that are independently selected and include, but are not limited to, hydrogen, $C_{1-6}$alkyl, aryl, $C_{1-6}$alkylaryl, $C_{3-8}$cycloalkyl, heterocycle, heteroaryl, $C_{1-6}$alkylhydroxy, $C_{1-6}$alkoxy and $NR^4R^4$.

In a preferred embodiment, R is a 6-membered aromatic ring containing 2 nitrogen atoms. In another preferred embodiment, R is a 6,5-fused aromatic ring containing from 1–4 nitrogen atoms. In yet another preferred embodiment, R is a 6,6-fused aromatic ring containing from 1–4 nitrogen atoms.

In another embodiment, R is a functional group including, but not limited to, the following:

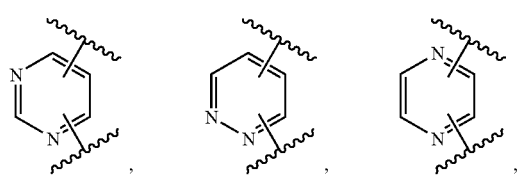

-continued

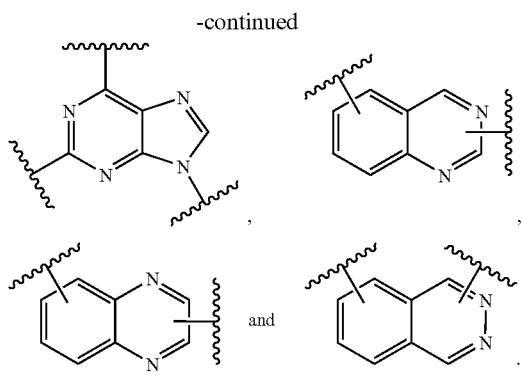

In still another preferred embodiment, R is a functional group including, but not limited to, the following:

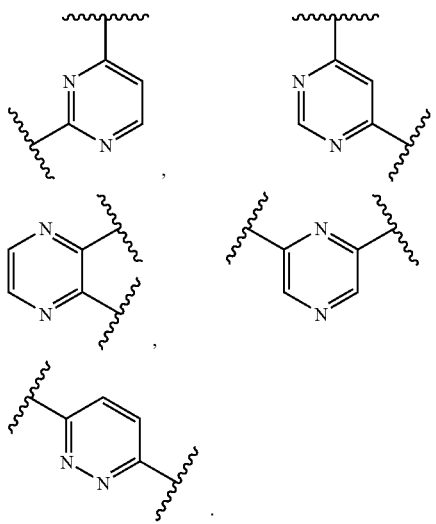

In yet another preferred embodiment, R is a functional group including, but not limited to, the following:

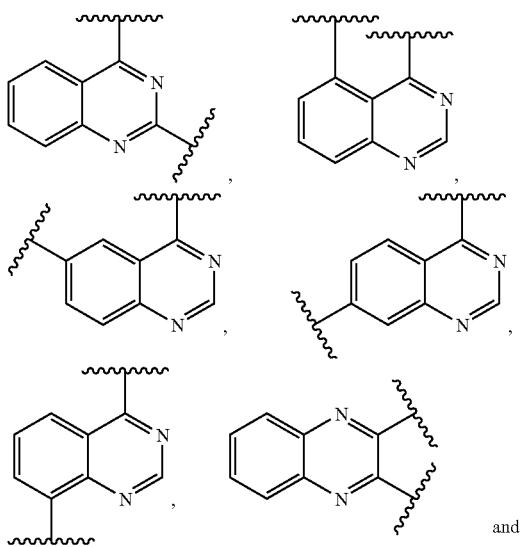

-continued

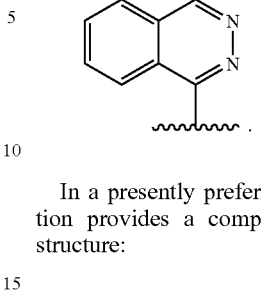

In a presently preferred embodiment, the present invention provides a compound wherein R is the following structure:

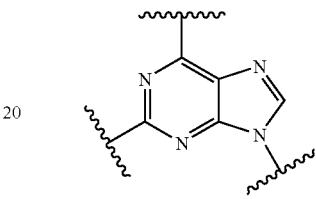

In another embodiment, the present invention provides a compound wherein R is a 2,6,9-substituted purine, substituted with a functional group including, but not limited to, the following:

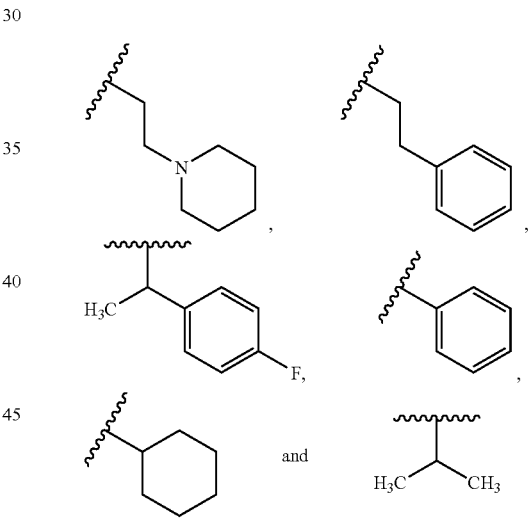

In Formula XV, $R^1$ is a functional group including, but not limited to, phenyl and benzyl, substituted on the aromatic ring with from 1–4 substituents that are independently selected and that include, but are not limited to, $C_{1-6}$alkyl, $C_{1-6}$alkoxy, $C_{1-6}$alkylhydroxy, $C_{1-6}$alkylamine, $C_{1-6}$aminoalkyl, halo and heterocycle. In a preferred embodiment, $R^1$ is a phenyl substituted with a morpholino group.

L, in Formula XV, is a functional group including, but not limited to, —O—, —$NR^2$— and a bond. In a presently preferred embodiment, L is —O—.

In Formula XV, each $R^2$ is independently selected and is a functional group including, but not limited to, hydrogen and $C_{1-4}$alkyl. In a preferred embodiment, $R^2$ is hydrogen or methyl.

$R^3$, in Formula XV, is a functional group including, but not limited to, hydrogen, optionally substituted alkyl, optionally substituted heteroalkyl, optionally substituted aryl, optionally substituted heteroaryl, optionally substituted heterocycloalkyl, halogen and alkoxy groups.

In an alternative embodiment, $R^2$ and $R^3$ can be taken together to form a 3–8 membered heterocyclic ring containing from 1–2 heteroatoms that are independently selected from N and O, and that are optionally substituted with 1–2 substitutents that are independently selected and include, but are not limited to, $C_{1-4}$alkyl, $C_{1-4}$alkylhydroxy, $C_{1-4}$alkoxy and $C_{1-4}$alkylamine.

$R^4$, if present in Formula XV, is a functional group including, but not limited to, optionally substituted alkyl, optionally substituted heteroalkyl and acyl groups.

In a preferred embodiment, the present invention provides a compound wherein R is a 2,6,9-substituted purine, substituted with a member selected from the group consisting of:

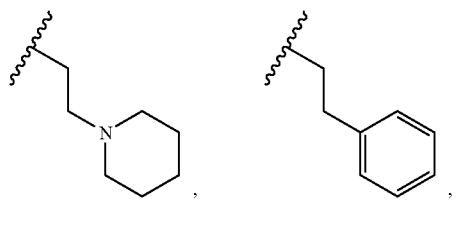

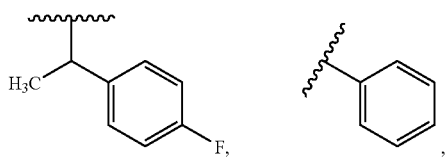

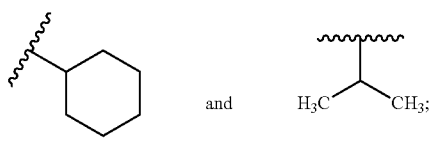

$R^1$ is a phenyl substituted with morpholine, i.e., a morpholino group;

L—$R^3$ is a member selected from the group consisting of:

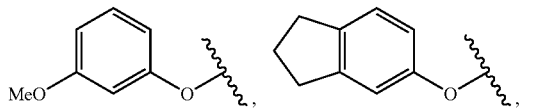

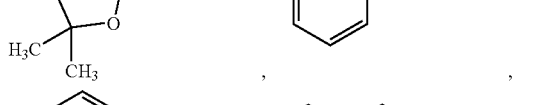

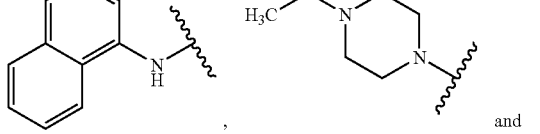

-continued

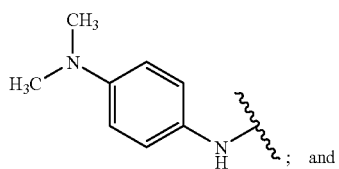

$R^4$ is not present or, if present, $R^4$ is isopropyl.

Illustrative compounds of the present invention include, but are not limited to, the following:

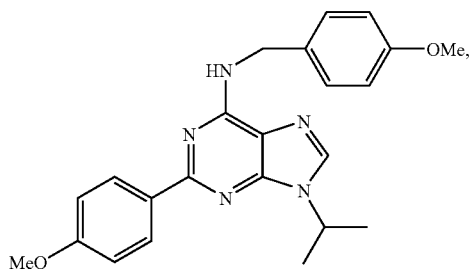

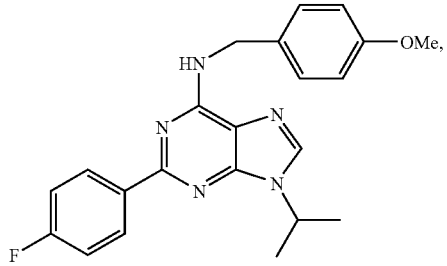

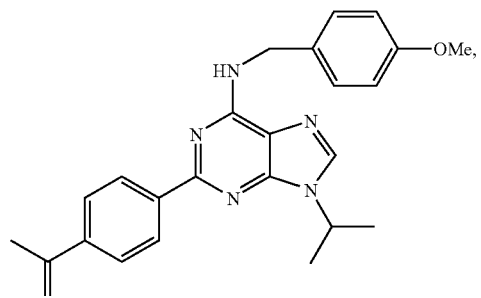

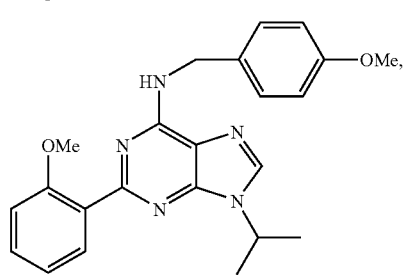

-continued
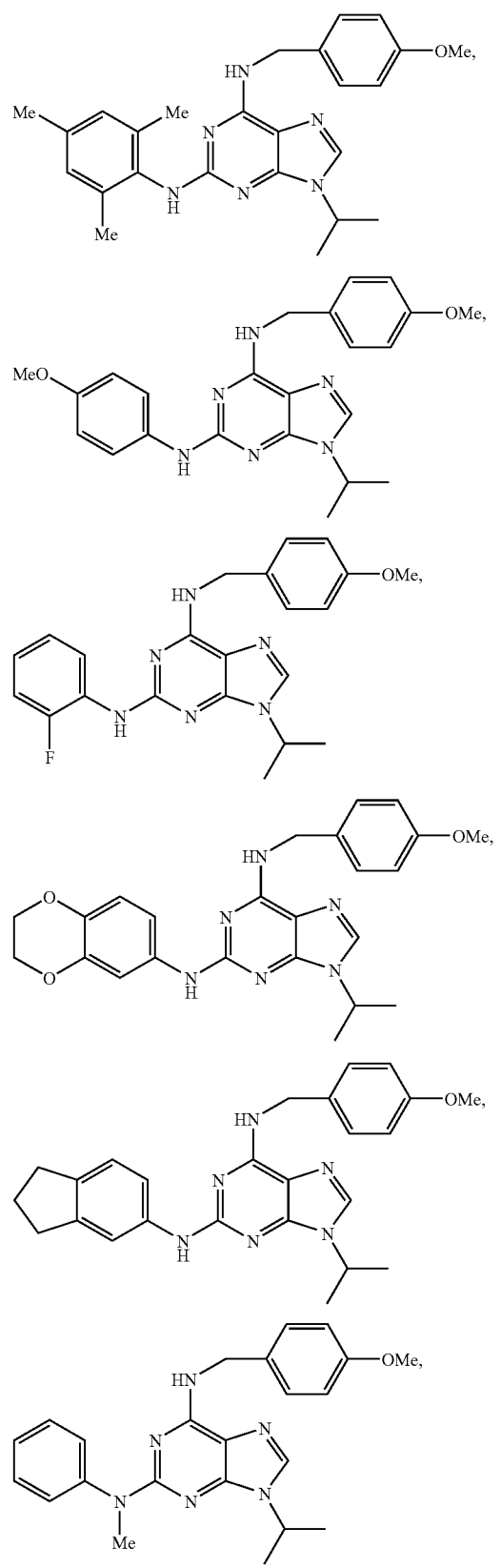
-continued
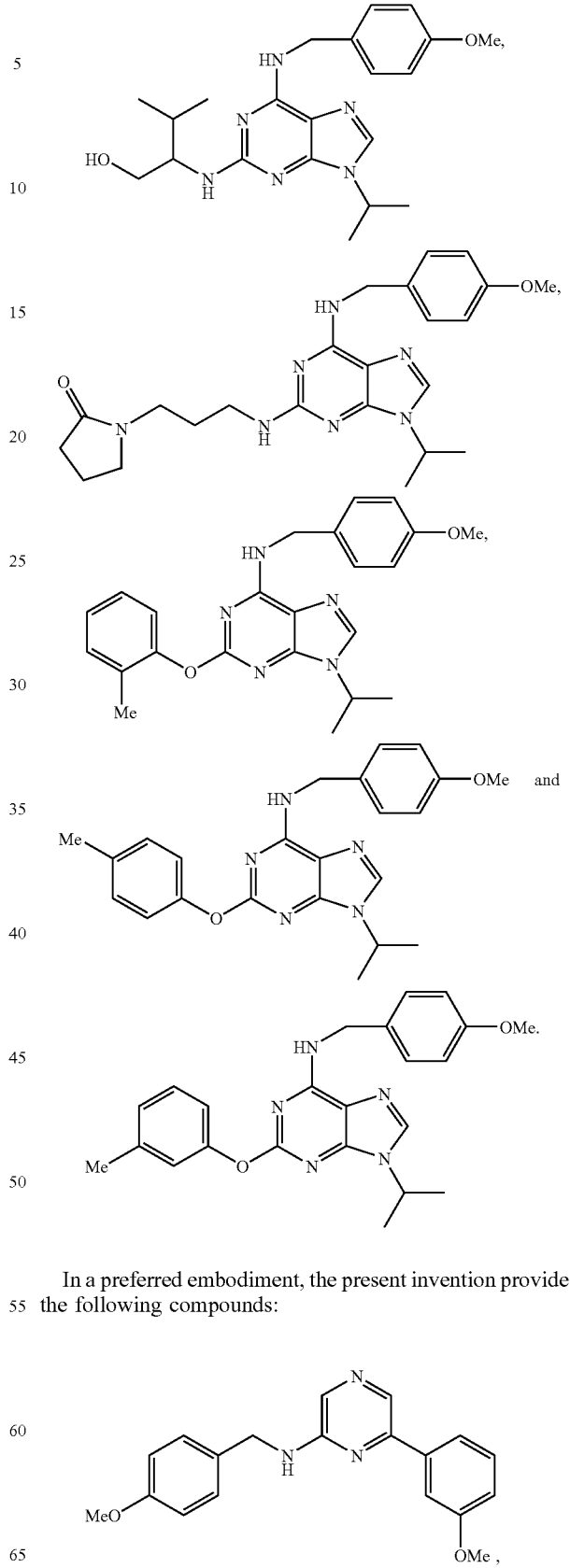
In a preferred embodiment, the present invention provides the following compounds:
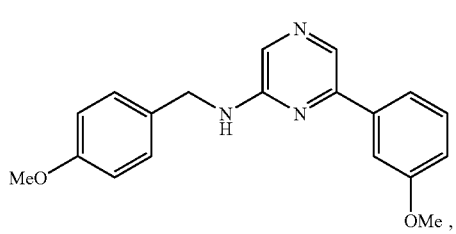

-continued

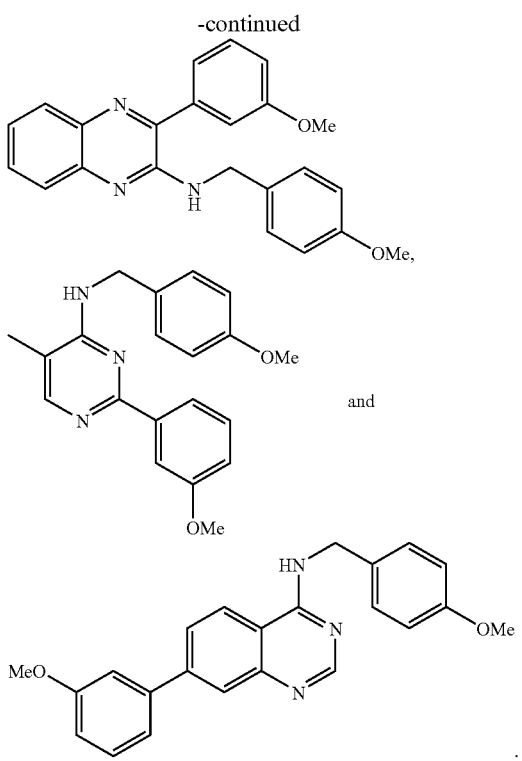

and

The compounds of the present invention can exist as geometric isomers, most notably when olefins (carbon-carbon double bonds) are incorporated. The invention includes the individual geometric isomers as well as mixtures of isomers. When an asymmetric center is incorporated in a compound of the present invention, it can exist as a pair of optical isomers. The invention includes the individual optical isomers as well as mixtures thereof. When a compound of the present invention contains multiple asymmetric centers, multiple centers of geometric isomerism, one or more centers of geometric isomerism in addition to one or more asymmetric centers, the invention includes all combinations of geometric and optical isomers.

The compounds of the present invention can exist as neutral compounds or as acid addition salts. The invention includes both the neutral and salt forms. It specifically contemplates pharmaceutically acceptable acid addition salts, including salts formed with inorganic acids such as hydrochloric acid, hydrobromic acid, sulfuric acid, phosphoric acid, and the like, and salts formed with organic acids such as acetic acid, citric acid, fumaric acid, maleic acid, benzoic acid, methanesulfonic acid, and the like. The invention encompasses hydrated forms and solvated forms of the compounds of the present invention and of their acid addition salts.

Where a carboxylic acid is included, the compounds of the present invention can exist as neutral compounds or as salts, where the carboxylate anion in paired with an organic or inorganic counterion. The counterion can be an external cationic species, or it can be an ammonium group present within the compounds of the present invention, in which case the molecule is zwitterionic. The invention includes the neutral and salt forms, including zwitterionic forms. It specifically contemplates pharmaceutically acceptable salts, including salts formed with inorganic counterions such as lithium, sodium, potassium, ammonium, and the like, and salts formed with organic counterions, such as alkylammonium, dialkylammonium, trialkylammonium, tetralkylammonium, trialkylsulfonium, tetraalkyl or tetraaryl phosphonium counterions and the like. The invention encompasses hydrated forms and solvated forms of the compounds of the present invention and of their carboxylate salts when a carboxylic acid group is present.

The compounds of the present invention can be readily screened for their kinase inhibitory activity, i.e., their ability to inhibit kinases, using in vitro and in vivo assays known to those of skill in the art. For instance, purine analogs having protein kinase inhibitory activity can be screened for using the CDK2/CYCLIN A microtiter-based solution-phase protein kinase assay described by Buxbaum, J. D., et a.l, Anal. Biochem,. 169:209–215 (1988), the teachings of which are incorporated herein by reference.

Methods

The present invention provides, inter alia, methods for the solution phase and solid phase synthesis of substituted heteroaryls and, in particular, substituted purines. In particular, the present invention provides methods for the solution phase synthesis of substituted heteroaryls (such as substituted purines) as well as methods for the solid phase synthesis of substituted heteroaryl scaffold moieties (such as substituted purine moieties). The present invention further provide methods for the preparation of a chemical library or array of substituted heteroaryl scaffold moieties through the application of solid-support media.

a) Solution Phase Synthesis of Substituted Heteroaryls (e.g., Substituted Purines)

In one aspect, the present invention provides a method of preparing a C2-substituted purine compound, the method comprising: reacting a C2-halogenated purine compound with a compound of Formula I:

$$A\text{—}X \qquad\qquad I$$

in the presence of a solvent, a base, a carbene or phosphine ligand and a palladium catalyst to provide the C2-substituted purine compound. In Formula I, A is a functional group including, but not limited to, alkyl, substituted alkyl, aryl, substituted aryl, heterocyclyl and substituted heterocyclyl; and X is a functional group including, but not limited to, —B(OH)$_2$, —OH, and —NHR$^1$, wherein R$^1$ is a functional group including, but not limited to, hydrogen, alkyl and substituted alkyl.

In a preferred embodiment the C2-substituted purine compound is a compound of Formula II:

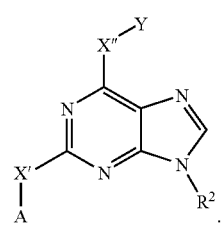

In Formula II, R$^2$ is a functional group including, but not limited to, hydrogen, alkyl, substituted alkyl, aryl, substituted aryl, heterocyclyl and substituted heterocyclyl;

X', in Formula II, is a functional group including, but not limited to, a bond, NR¹ and O, wherein R¹ is as defined above.

X", in Formula II, is a functional group including, but not limited to, a bond, O and NR³, wherein R³ is a functional group including, but not limited to, hydrogen, alkyl and substituted alkyl, with the provisos that when X" is NR³, Y is R⁴ or A', and that when X' is O or a direct bond, Y is A'.

In Formula II, A is as defined above, whereas A' is a functional group including, but not limited to, alkyl, substituted alkyl, aryl, substituted aryl, arylalkyl, substituted arylalkyl, heterocyclyl and substituted heterocyclyl.

If Y is R⁴, R⁴ is a functional group including, but not limited to, alkyl or substituted alkyl.

In a preferred embodiment, the C2-halogenated purine is a compound having the structure of Formula III:

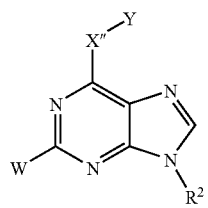

III

In Formula III, W is a halogen, i.e., a halo group, including, but not limited to cholor, fluoro, bromo and iodo. In a presently preferred embodiment, W is a chloro or fluoro group. In Formula III, X", Y and R² are as defined above. In a presently preferred embodiment, W is chloro; R² is isopropyl; X" is NR³, wherein R³ is hydrogen; and A' is methoxybenzyl.

In one preferred embodiment, the present invention provides a method of preparing a C2-substituted purine compound of Formula II:

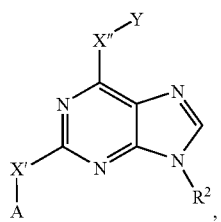

II the method comprising: reacting a C2-halogenated purine compound of Formula III:

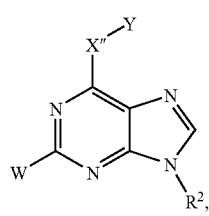

III with a compound of Formula I:

A—X      I, in the presence of a solvent, a base, a carbene or phosphine ligand and a palladium catalyst, thereby forming the compound of Formula II.

In the compounds of Formulae I, II and III of the above method, W, X, X' X", A, A', Y, R¹, R², R³, R⁴ are as defined above.

In the above methods, carbene or phosphine ligands can be used. Examples of ligands suitable for use in the methods of the present invention include, but are not limited to, the following carbene and phosphine ligands:

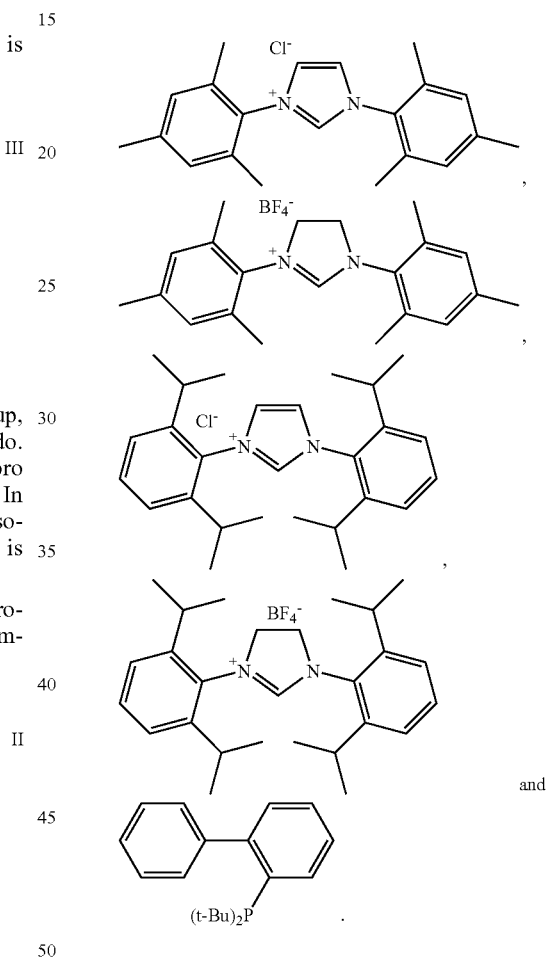

and

In a presently preferred embodiment, the ligand is a carbene ligand including, but not limited to, the following:

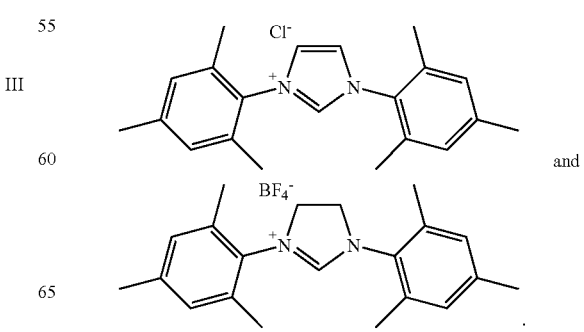

and

A number of bases can be used in carrying out the methods of the present invention. Examples of bases suitable for use in the above method include, but are not limited to, cesium carbonate, potassium carbonate, sodium carbonate, sodium bicarbonate, potassium bicarbonate, cesium bicarbonate, potassium fluoride, potassium phosphate, potassium tert-butyloxide, sodium tert-butyloxide, and triethylamine.

A number of solvents can be used in carrying out the methods of the present invention. Examples of solvents suitable for use in the above method include, but are not limited to, 1,4-dioxane, tetrahydrofuran, dimethoxyethane (DME), dimethylformamide (DMF), benzene and toluene.

A number of palladium catalysts can be used in carrying out the methods of the present invention. Typically, the oxidation state of the palladium in the catalyst is (0) or (II). Examples of palladium catalysts suitable for use in carrying out the methods of the present invention include, but are not limited to, $Pd_2(dba)_3$, $Pd(OAc)_2$, $Pd(PPh_3)_4$, Pd(O), $PdCl_2$(dppf) and $PdCl_2$. Such catalysts are known to and used by those of skill in the art and, thus, their structures are known. In a preferred embodiment, the palladium catalyst is $Pd_2(dba)_3$.

In another embodiment, the present invention provides a method for preparing a compound of Formula III, the method comprising: reacting a dihalopurine, such as the compound of Formula IV:

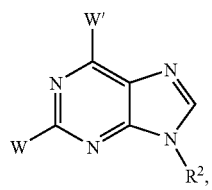

IV with a compound of Formula V:

X'''—A'  V, in the presence of a solvent, a base, a carbene or phosphine ligand and a palladium catalyst, thereby forming the compound of Formula III.

In the above method, W and W' are both halogen; X''' is a functional group including, but not limited to, $-B(OH)_2$, —OH and $NHR^3$, wherein $R^3$ is a functional group including, but not limited to, hydrogen, alkyl and substituted alkyl. In a preferred embodiment, W and W' are both chloro or both fluoro.

In a preferred embodiment, the present invention provides a chemical library comprising a plurality of 2-substituted purine compounds prepared by the methods described above.

In another aspect, the present invention provides a method for preparing a C6-substituted purine compound, the method comprising: reacting a C6-halogenated purine with a compound of Formula I:

A—X  I, in the presence of a solvent, a base, a carbene or phosphine ligand and a palladium catalyst to provide the C6-substituted purine compound. In Formula I, A is a functional group including, but not limited to, alkyl, substituted alkyl, aryl, substituted aryl, heterocyclyl and substituted heterocyclyl; and X is a functional group including, but not limited to, $-B(OH)_2$, —OH, and $-NHR^1$, wherein $R^1$ is a functional group including, but not limited to, hydrogen, alkyl and substituted alkyl.

In a preferred embodiment the C6-substituted purine compound is a compound of of Formula VI or Formula VII:

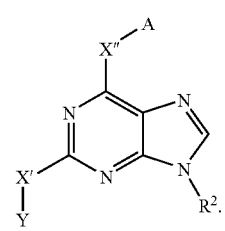

VI

In Formula VI, $R^2$ is a functional group including, but not limited to, hydrogen, alkyl, substituted alkyl, aryl, substituted aryl, heterocyclyl and substituted heterocyclyl.

X', in Formula VI, is a functional group including, but not limited to, a bond, $NR^1$ and O, wherein $R^1$ is a functional group including, but not limited to, hydrogen, alkyl and substituted alkyl.

X", in Formula VI, is a functional group including, but not limited to, a bond, O and $NR^3$, wherein $R^3$ is a functional group including, but not limited to, hydrogen, alkyl and substituted alkyl, with the proviso that when X" is $NR^3$, Y is $R^4$ or A', and when X is O or a direct bond, Y is A'.

In Formula VI, A is a functional group including, but not limited to, alkyl, substituted alkyl, aryl, substituted aryl, heterocyclyl and substituted heterocyclyl, whereas A' is a functional group including, but not limited to, alkyl, substituted alkyl, aryl, substituted aryl, arylalkyl, substituted arylalkyl, heterocyclyl and substituted heterocyclyl;

$R^4$, in Formula VI, is a functional group including, but not limited to, alkyl or substituted alkyl.

In a presently preferred embodiment, the C6-halogenated purine is a compound of Formula VII:

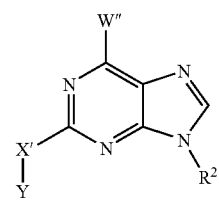

VII

In Formula VII, W is a halogen or halo group (e.g., chloro, fluoro, bromo or iodo), whereas X' and Y are as defined above.

In another aspect, the present invention provides a method for preparing a C6-substituted purine compound of Formula VI:

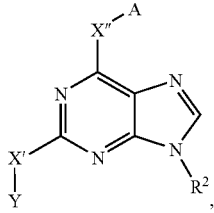

VI

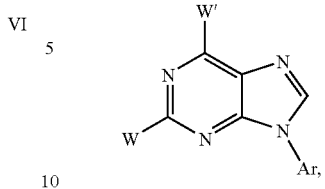

IX the method comprising: reacting a C6-halogenated purine of Formula VII:

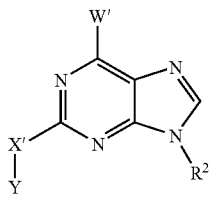

VII with a compound of Formula I:

 A—X    I, in the presence of a solvent, a base, a carbene ligand and a palladium catalyst to provide a C6-substituted purine compound of Formula VI.

In a presently preferred embodiment, the present invention provides a chemical library comprising a plurality of 6-substituted purine compounds prepared by the methods described above.

It is noted that the discussion (as well as preferred embodiments) relating to the carbene or phophine ligands, bases, solvents and palladium catalysts set forth in connection with the method for preparing a C-2 substituted purine compound are fully applicable to the method for preparing a C-6 substituted purine compound and, thus, it will not be repeated here.

In yet another embodiment, the present invention provides a method for preparing a 9-aryl substituted purine compound, the method comprising: reacting a 2,6-dihalogenated purine with a compound of Formula X:

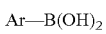 Ar—B(OH)$_2$    X, in the presence of a solvent and a catalyst, to provide the 9-aryl substituted purine compound.

In Formula X, Ar is a functional group including, but not limited to, aryl, substituted aryl, heterocyclyl and substituted heterocyclyl.

In a presently preferred embodiment, the 9-aryl substituted purine compound is a compound of Formula IX:

In Formula IX, Ar is a functional group including, but not limited to, aryl, substituted aryl, heterocyclyl and substituted heterocyclyl. W and W', in Formula IX, are each independently selected and include, but are not limited to, fluoro, chloro, bromo and iodo.

In a preferred embodiment of the foregoing method, the catalyst is a copper catalyst. Suitable copper catalysts for use in the present invention will be known to and used by those of skill in the art. Typically, the copper of the copper catalyst is in an oxidation state of (0), (I) or (II). Examples of copper catalysts suitable for use in the method of the present invention include, but are not limited to, Cu(OAc)$_2$, [Cu(OH).TMEDA]$_2$Cl$_2$ and CuI. In a presently preferred embodiment, the catalyst is cupric acetate.

A number of solvents can be used in carrying out the methods of the present invention. Examples of solvents suitable for use in the above method include, but are not limited to, 1,4-dioxane, tetrahydrofuran, dimethoxyethane (DME), dimethylformamide (DMF), benzene and toluene.

In a presently preferred embodiment, the present invention provides a chemical library comprising a plurality of 9-aryl substituted purine compounds prepared by the methods described above.

b) Solid Phase Synthesis of Substituted Heteroaryls (e.g., Substituted Purines)

In yet another aspect, the present invention provides a method for synthesizing a substituted heteroaryl, the method comprising: (a) providing a dihaloheteroaryl scaffold moiety; and (b) capturing the dihaloheteroaryl scaffold moiety on a resin by nucleophilic substitution of a first halogen by a resin-bound amine nucleophile to afford a substituted heteroaryl, e.g, a resin-bound amine substituted monohaloheteroaryl.

Suitable resins useful for the present invention include, but are not limited to, PAL resin, Wang resin, and polystyrene resin. Other suitable resins would be clear to a person of skill in the art. In a preferred embodiment, the PAL resin is utilized.

In a preferred embodiment, the two halogens, i.e., halo groups, of the dihaloheteroaryl scaffold moiety are independently selected and include, but are not limited to, chloro, fluoro, bromo and iodo. In a presently preferred emodiments, the two halogens are chloro or fluoro groups.

In a preferred embodiment, the method further comprises substitution of the second halogen of the dihaloheteroaryl scaffold moiety by nucleophilic displacement or, alternatively, by a coupling reaction. In a presently preferred embodiment, a coupling reaction is employed to carry out the substitution of the second halogen of the dihaloheteroaryl scaffold moiety. In this connection, the coupling reaction is preferably a palladium-mediated coupling reaction.

It will be readily apparent to those of skill in the art that the two halogens, i.e., halo groups, of the dihaloheteroaryl scaffold moiety can be substituted with a number of different functional groups. Suitable functional groups include, but are not limited to, anilines, phenols, amines and boronic acids (see, Table 1). In a preferred embodiment, the functional group includes, but is not limited to, aryl boronic acids, anilines and phenols.

In a preferred embodiment, the method further comprises performing an initial substitution prior to substitution of the first halogen of the dihaloheteroaryl scaffold moiety. In a preferred embodiment, the initial substitution is carried out using a reaction including, but not limited to, alkylation reactions, acylation reactions and coupling reactions.

Numerous dihaloheteroaryl scaffold moieties can be used in the methods of the present invention. Examples of suitable dihaloheteroaryl scaffold moieties include, but not limited to, purines, pyrimidines, quinazolines, pyrazines, phthalazines, pyradazines and quinoxalines.

When a palladium-catalyzed coupling reaction is employed to substitute the halo groups of the dihaloheteroary or the halo group of the resin-bound amine substituted monohaloheteroaryl, the palladium-catalyzed coupling reaction typically involves reacting the dihaloheteroaryl or the resin-bound amine substituted monohaloheteroaryl with a coupling agent in the presence of a solvent, a palladium catalyst, a base and a carbene or phosphine ligand. Suitable coupling agents include, but are not limited to, boronic acids, amines and alcohols. In a presently preferred embodiment, suitable coupling agents include, but are not limited to, aryl boronic acids, anilines and phenols. It is noted that the foregiong discussions relating to the carbene or phophine ligands, bases, solvents, palladium catalysts and copper catalysts set forth in connection with the methods for preparing a C-2 substituted purine compound or a 9-aryl substituted purine compound are fully applicable to the method for preparing a substituted heteroaryl compound and, thus, they will not be repeated here.

In a preferred embodiment, the foregoing methods further comprise cleaving the compound from the solid support. It will be readily appreciated that the compounds of the present invention can be readily cleaved from the solid support using standard methods known to and used by those of skill in the art. Cleavage of a resin-bound compound nd liberation of the desired compound from the resin is typically carried in the presence of an acid. Suitable acids include, but are not limited to, an organic acid such as formic acid, acetic acid, propionic acid, trichloroacetic acid, trifluoroacetic acid and the like, and inorganic acids such as hydrochloric acid, hydrobromic acid, sulfuric acid, hydrogen chloride, etc., or the like. The reaction is usually carried out in a solvent such as water, an alcohol such as methanol, ethanol, 1,4, dioxane, methylene chloride, tetrahydrofuran, a mixture thereof or any other solvent which does not adversely influence the reaction.

In yet another aspect of the present invention, the foregoing method is adapted to prepare a library (or an array) of heteroaryl scaffold moieties. Typically, the library of substituted scaffold moieties is prepared using a plurality of dihaloheteroaryl scaffold moieties. As such, in another aspect, the present invention provides a method for synthesizing a combinatorial library of substituted heteroaryls (e.g., heterocycles), the method comprising: providing a plurality of dihaloheterocyclic scaffold moieties; and capturing the dichloroheterocyclic scaffold moieties on a resin by nucleophilic substitution of a first chlorine by a resin-bound amine nucleophile).

In a preferred embodiment, the two halogens, i.e., halo groups, present in the dihaloheteroaryl scaffold moieties are independently selected and include, but are not limited to, chloro, fluoro, bromo and iodo. In a presently preferred emodiments, the two halogens of the dihaloheteroary scaffold moieites are chloro groups.

In a preferred embodiment, the method further comprises substitution of the second halogen of the dihaloheteroaryl scaffold moieties by nucleophilic displacement or, alternatively, by a coupling reaction. In a presently preferred embodiment, a coupling reaction is employed to carry out the substitution of the second halogen of the dihaloheteroaryl scaffold moieties. In this connection, the coupling reaction is preferably a palladium-mediated coupling reaction.

It will be readily apparent to those of skill in the art that the two halogens, i.e., halo groups, of the dihaloheteroaryl scaffold moieties can be substituted with a number of different functional groups, each of which is independently selected. Suitable functional groups include, but are not limited to, anilines, phenols, amines and boronic acids (see, Table I). In a presently preferred embodiment, the functional groups include, but are not limited to, aryl boronic acids, anilines and phenols.

In a preferred embodiment, the method further comprises performing initial substitutions prior to substitution of the first halogens of the dihaloheteroaryl scaffold moieties. In a preferred embodiment, the initial substitution is carried out using a reaction including, but not limited to, alkylation reactions, acylation reactions and coupling reactions.

Numerous dihaloheteroaryl scaffold moieties can be used in the methods of the present invention. Examples of suitable dihaloheteroaryl scaffold moieties include, but not limited to, purines, pyrimidines, quinazolines, pyrazines, phthalazines, pyradazines and quinoxalines.

When a palladium-catalyzed coupling reaction is employed to substitute the halo groups of the dihaloheteroary scaffold moieties or the halo group of the resin-bound amine substituted monohaloheteroaryls, the palladium-catalyzed coupling reaction typically involves reacting the dihaloheteroaryl or the resin-bound amine substituted monohaloheteroaryl with a coupling agent in the presence of a solvent, a palladium catalyst, a base and a carbene or phosphine ligand. Suitable coupling agents include, but are not limited to, boronic acids, amines and alcohols. In a presently preferred embodiment, suitable coupling agents include, but are not limited to, aryl boronic acids, anilines and phenols. It is noted that the foregiong discussions relating to the carbene or phophine ligands, bases, solvents, palladium catalysts and copper catalysts set forth in connection with the methods for preparing a C-2 substituted purine compound or a 9-aryl substituted purine compound are fully applicable to the methods for preparing a combinatorial library or array of substituted heteroaryl compound and, thus, they will not be repeated here.

c) Illustrative Embodiments: Preparation of Libraries of Heteroaryl Scaffold Moieties via Solid Support Chemistry An exemplary strategy for preparing the scaffolds and inhibitors of the present invention relies on the capture of a dichloroheterocyclic scaffold (including substituted purines S1, pyrimidines S2, quinazolines S3, pyrazines S4, pyridazines S5, quinoxalines S6, phthalazines S7 and thiadiazoles S8) with a resin-bound amine nucleophile where one chloro group is susceptible to nucleophilic aromatic substitution. Depending on the type of heterocycle being captured, an initial alkylation, acylation or coupling reaction can be performed prior to the capture step to introduce one diversity element. The remaining chloro substituent is then available for nucleophilic displacement or a palladium-mediated coupling reaction with anilines, phenols, and boronic acids.

In an exemplary embodiment, the scaffolds and inhibitors of the invention are assembled using the procedure outlined in Scheme 1.

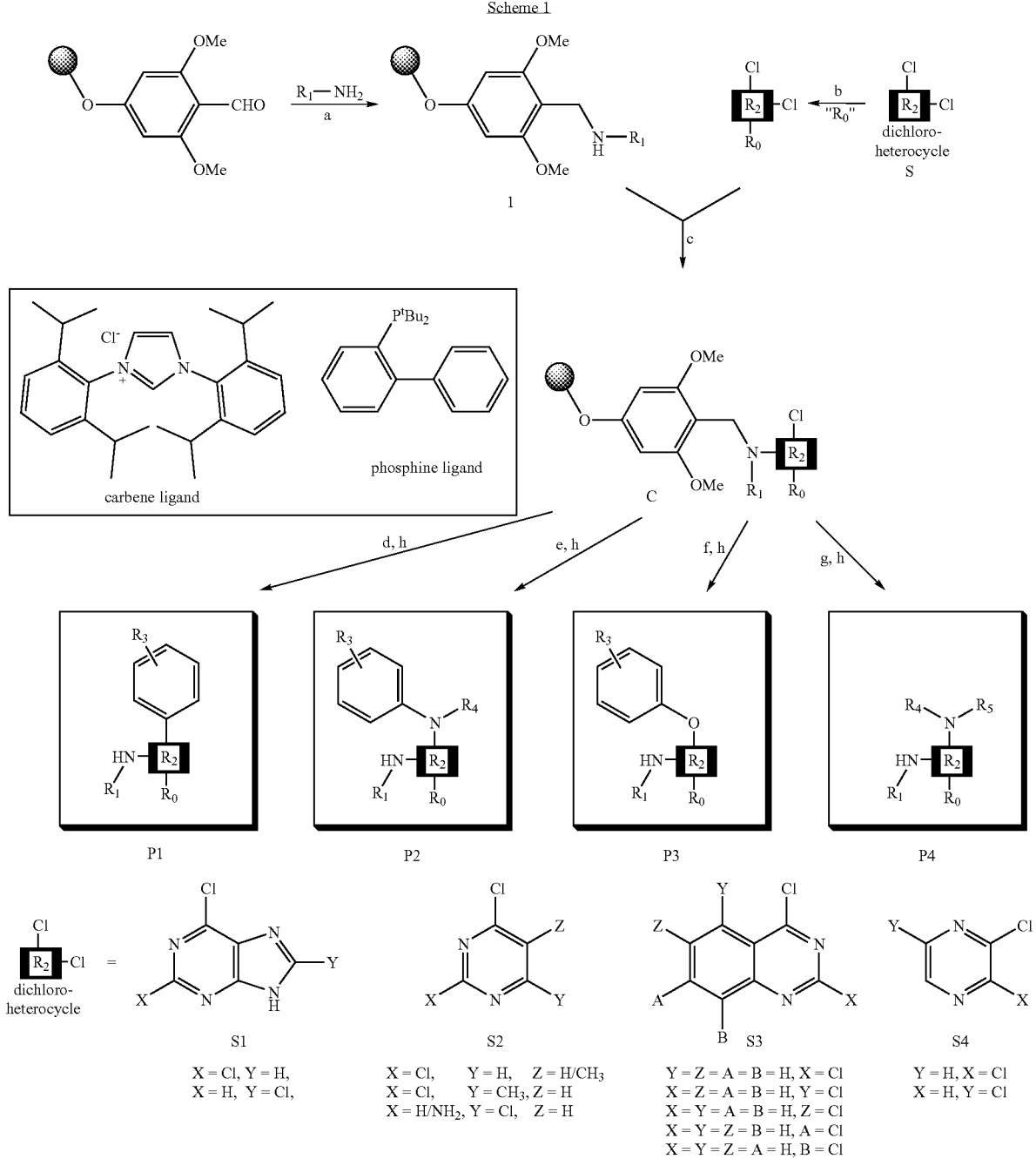

-continued

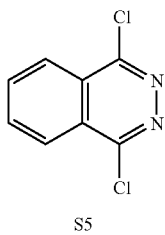
S5

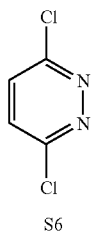
S6

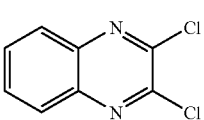
S7

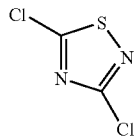
S8 a. NaBH(OAc)₃, 1% HOAc, THF; b. solution phase heterocycle modification: alkylation or acylation. c. DiEA, BuOH, 80° C., 12 hours;
d. 5 equiv of boronic acids, 7% of Pd₂(dba)₃, 14% of carbene ligand, 6 equiv of Cs₂CO₃, 1,4-dioxane, 90° C., 12 hours; e. 5 equiv of anilines,
7% of Pd₂(dba)₃, 14% of carbene ligand, 6 equiv of KO$^t$Bu, 1,4-dioxane, 90° C., 12 hours; f. 5 equiv of phenols, 7% of Pd₂(dba)₃, 28% of
phosphine ligand, 7 equiv of K₃PO₄, toluene, 90° C., 12 hours; g. 5 equiv of 1° or 2° amines, 90° C., 12 hours; h. CH₂Cl₂:TFA:Me₂S:H₂O/45:45:5:5

In an exemplary embodiment, the heterocycle capture strategy uses 2,6-dichloropurine because the 6-chloro can be selectively displaced by amines and the 2-chloro has been demonstrated to function in palladium-mediated coupling reactions in solution (see, U.S. Provisional Application No. 60/328,763, entitled "Expanding the Diversity of Purine Libraries," which was filed Oct. 12, 2001).

Suitable resins useful for the present invention would be clear to a person of skill in the art. In a preferred embodiment, a resin-bound nucleophilic amino group can be obtained through the coupling of primary amines to a (4-formyl-3,5-dimethoxyphenoxy)methyl-polystyrene resin (PAL-resin) by reductive amination using sodium triacetoxyborohydride with 1% acetic acid to afford the PAL-amine resin) (see, Albericio et al., *J. Org. Chem.*, 55, 3730 (1990); Boojamra et al., *J. Org. Chem.*, 62, 1240 (1997); and Jin et al., *J. Comb. Chem.*, 3, 97 (2001)). The PAL linkage offers the advantage that functionalized amines can readily be installed and cleavage results in an NH group that serves as a key hydrogen bond donor to many kinase active sites. A representative sequence starts by loading 2,6-dichloropurine onto the PAL-amine at the more reactive C6 position in butanol at 80° C. with exclusive regioselectivity. Modification of the N9 position of purine can be achieved by either Mitsunobu alkylation of N9 on a solid support (Path B) or by capturing the product of a solution phase Mitsunobu alkylation of 2,6-dichloropurine (Path A, Scheme 2). The latter approach offers the advantages of using less reagents and ease of handling. However, alkylation on a solid support provides improved regio-selectivity (N9/N7), presumably because N7 is more sterically hindered due to the presence of a large substituent at C6. Having the flexibility to perform the alkylation either on a solid support or in solution offers different operational advantages when making large combinatorial libraries. Most primary and secondary alcohols lacking additional acidic hydrogens work well in the Mitsunobu reaction at N9 (see, Chang et al., *Chemistry and Biology*, 6, 361 (1999); and U.S. Provisional Application No. 60/328,741, entitled "A Concise and Traceless Linker Strategy Toward Combinatorial Libraries of 2,6,9-Substituted Purines," which was filed Oct. 12, 2001).

In another exemplary embodiment, a palladium-catalyzed cross-coupling step can be performed as, for example, a final derivatization process, as illustrated in Scheme 2.

Scheme 2

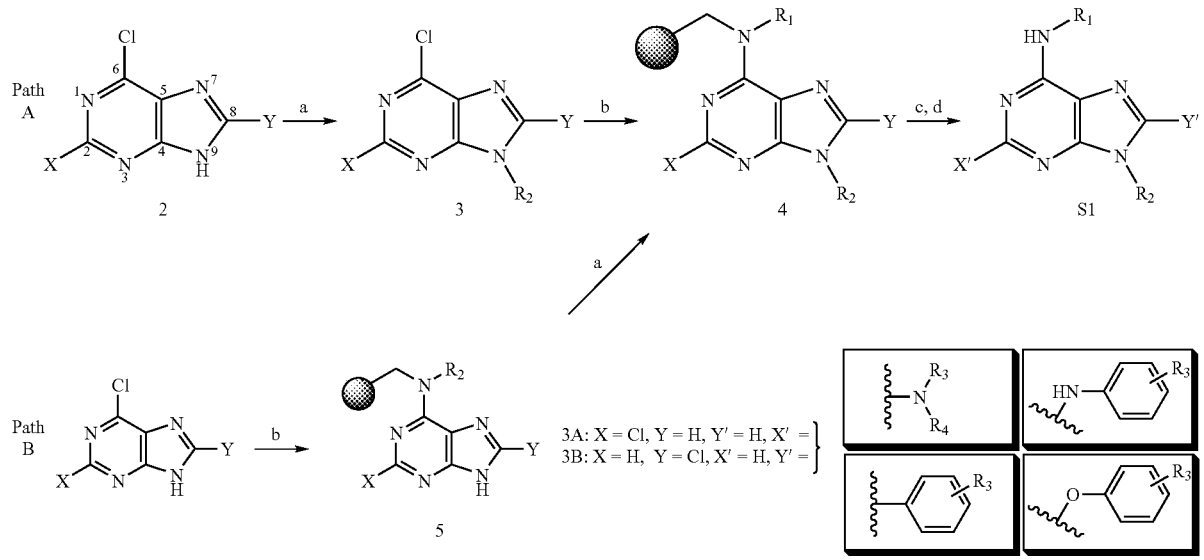

a. 1.5 equiv of R₂OH, 2 equiv of PPh₃, 1.3 equiv of DiAD, THF, RT; b. 0.5 equiv of 1, 1.5 equiv DiEA, BuOH, 80° C.,
c. 5 equiv of boronic acids/amines/phenols, 7% of Pd₂(dba)₃, 14% of carbene ligand for coupling with boronic acids,
anilines and amines/or 28% phosphine ligand for coupling with phenols, Cs₂CO₃, KO^tBu and K₃PO₄ for coupling
with boronic acids, aniline/amines and phenols respectively; d. CH₂Cl₂:TFA:Me₂S:H₂O/45:45:5:5

As illustrated in Scheme 2, a palladium-catalyzed cross-coupling reaction is performed as the final derivatization step. An exemplary embodiment utilizes approximately five equivalents of the coupling partner (arylboronic acids, anilines or phenols), 7 mol % of Pd₂(dba)₃, 14 mol % of the corresponding ligand and six equivalents of the base. The resulting mixture is maintained for 12 hours at 80° C. with 1,4-dioxane for C—C and C—N bond formation or toluene for C—O bond formation as solvent. Although the reaction time and the amount of coupling reagents can be optimized for each type of reaction and substrate, the general coupling protocol described above is generally useful for achieving quantitative conversion of the starting material (the chloro-group at the C2 position of purine) with different substrates on the solid support.

The palladium catalyzed cross-coupling reaction can also be used to prepare heterocycloalkyl and heteroaryl moieties having an array of substituents appended thereto. For example, resin-bound purine 3 (X=Cl, Y=H, Scheme 2) can be reacted with a variety of arylboronic acids, anilines/amines, and phenols. See, Table 1. Analysis of the products following TFA mediated cleavage by LC-MS revealed greater that 95% conversion with a variety of electron rich or poor aromatic ring systems. The amination reaction proved to be the most versatile with diverse substrates ranging from primary and secondary anilines to a sterically hindered primary amine (2-amino-3-methyl-butanol) and cyclic/acyclic secondary amines (see Table 1). While all three types of palladium-catalyzed cross-coupling reactions on solid support were preferentially carried out in concentrated form (>0.2M), the amination reaction is preferably performed with at least 0.2 M aniline otherwise a significant amount of t-butoxide substituted product can be observed.

TABLE 1

| Boronic Acids | Anilines | Amines | Phenols |
|---|---|---|---|
| 4-F-C₆H₄ | HN-C₆H₄-OCH₃ | HN-CH(iPr)-CH₂OH | 2-CH₃-C₆H₄-O |
| 2-OCH₃-C₆H₄ | HN-benzodioxane | HN-(CH₂)₃-N-pyrrolidinone | 3-CH₃-C₆H₄-O |

TABLE 1-continued

| Boronic Acids | Anilines | Amines | Phenols |
|---|---|---|---|

The palladium catalyzed C2-couplings on solid support can be extended to the reaction to C-8 halo-substituted purines (e.g., C-8 bromo or chloro-substituted purines). In an exemplary embodiment, the C-8 bromo/chloro substituted purines are prepared by lithiation of the C8 position of 6-chloro-9-tetrahydropyranyl or 2,6-dichloro-9-tetrahydropyranyl purine with LDA followed by quenching with appropriate halogen donors. The tetrahydropyranyl protecting group can be removed by treatment with 10% acetic acid in methanol. After Mitsunobu alkylation of N9 and resin capture at C6, the support-bound purines can be modified at C8 or C2 and C8 simultaneously using palladium-mediated cross-coupling reactions as described above (see, Scheme 2). This chemistry provides access to known adenosine-P1 receptor antagonists as well as generic 6–5–6 triaryl systems that represent a large class of bioactive pharmacophores.

The heterocycle resin-capture strategy of the present invention has broad general applicability. For example, a collection of dichloroheterocycles can be coupled to PAL-amine resin. The general resin capture condition involves reacting 2 equivalents of dichloroheterocycles with PAL-amine in the presence of 3 equivalents of diisopropylethylamine at 90° C. in butanol for 24 hours. Because the resin-capture presumably proceeds through a nucleophilic aromatic substitution mechanism, electron poor dichloroheterocycles are loaded on solid support quantitatively using the reaction condition described above. These include all the heterocycles shown in Scheme 1.

According to the present invention certain heterocycles, such as 2,4-dichloropyrimidine are captured at room temperature with high efficiency. The capture of other heterocycles is possible using the methods set forth herein. Different scaffolds can require different conditions for efficient capture to occur. For example, S4 to S6 require more forcing conditions (90° C., n-butanol, 24 hrs., quantitative loading) than 2,4-dichloropyrimidine. Determining suitable capture conditions for a particular heterocycloalkyl or heteroaryl group is well within the abilities of those of skill in the art.

Using the methods set forth herein, it is possible to obtain regioselective capture of a scaffold. For example, 2,4-dichloropyrimidine resulted in a regioisomeric mixture with some resin-bound amines, e.g., PAL-resin-bound primary amines capture 2,4-dichloropyrimidine exclusively at C4 position. The palladium-catalyzed amination conditions provided herein can be used to carry out resin-capture of less electron poor dichloroheterocycles with moderate loading.

Following capture of the dichloroheterocycles on the solid support, the remaining chloro substituent is generally replaced by another group. In one embodiment, the chloro group is replaced in a palladium-catalyzed cross-coupling reaction. In an exemplary embodiment, $R_1$ was fixed as p-methoxybenzylamine and the remaining chloro group of the resin-captured heterocyclic scaffolds was subjected to a palladium-catalyzed cross-coupling reaction as the final derivatization step. The reaction conditions are essentially the same as described for the purines. These conditions are general for both modifying the whole spectrum of resin-captured heterocycles with all regioisomers and achieving quantitative conversion of the starting material (the remaining chloro-group) with different substrates on the solid support. While the yields of the cleaved final products mainly depend on the capture step which can be achieved quantitatively using the standardized capture condition described above (since quantitative palladium catalyzed final derivatization can be easily achieved), little impurities sometimes appeared when the qualities of coupling substrates (boronic acids, anilines and phenols) varied. For example, up to 5% of de-halogenation product could be observed when the substrates are somewhat wet. Removal of small amounts of impurity is within the abilities of those of skill in the art by methods such as recrystallization, chromatography, extraction and the like.

In some embodiments, it has been found that the use of resin-bound amino alcohol, such as ethanolamine derivatives, results in intramolecular cyclization products under the palladium catalyzed C—C or C—O bond formation condition even with excess boronic acids or phenols around where the oxygen atom of the resin-bound amino alcohol displaces the proximal remaining chloro group of the heterocycle to form 6 or 7-membered ring system.

In another exemplary embodiment, the chloro group is replaced using nucleophilic aromatic substitution conditions. The less reactive C2-chloro group of pyrimidine (S2), quinazoline (S3) and C3-chloro of thiadiazole (S8) reacts with various amines quantitatively. Preferred conditions include high concentration (>2M) amine and reactions times of about 12 hours at 100° C.

In yet another exemplary embodiment, anilines react with the C2 chloro group of pyrimidine scaffold. Preferred conditions are 0.2M of the aniline at 80° C. The C6-chloro group of pyrimidine and the second chloro group of scaffolds S4 through S7 can react quantitatively with anilines in the presence of a stoichiometric amount of potassium t-butoxide as the base.

As only a small subset of the heterocycles could be modified under standard nucleophilic aromatic substitution conditions, the use of palladium-catalyzed cross-coupling reactions on solid support was investigated. With $R_1$ fixed as p-methoxybenzylamine, the remaining chloro group of the resin-captured heterocyclic scaffolds was subjected to a palladium-catalyzed cross coupling reaction as the final derivatization step. The reaction conditions are essentially the same as described for the purines. These conditions were found to be most general for modifying the resin-captured heterocycles (see, Table 2) and generally afforded quantitative conversion of the starting material (the remaining chloro group) with different substrates on the solid support. Exploration of the reaction scope revealed the same broad range of substrates can be used as demonstrated for the purine scaffold (see Table 1). A survey of resin-bound amines also showed considerable diversity in primary amines that are effective substrates. Only β-branched resin-bound primary amines were found to have relatively slow capture rates. Interestingly, the use of resin-bound amino alcohols, such as ethanolamine derivatives, can provide intramolecular cyclization products for 2,3-dichloroquinoxaline and 2,3-dichloropyrazine under the palladium-catalyzed C—C or C—O bond formation conditions to form six- or seven-membered ring systems (Torraca et. al., *J. Am. Chem. Soc.*, 122, 12907–12908) (2000) (Scheme 3).

TABLE 2

Validation of Heterocyclic Scaffolds as Diversity Inputs

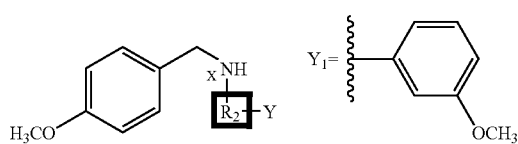

| Entry | Scaffolds ($R_2$) | ($Y_1$) Purity & Yield (%) | ($Y_2$)Purity & Yield (%) | ($Y_3$)Purity & Yield (%) |
|---|---|---|---|---|
| 1 | 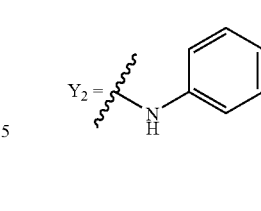 | 95 (90) | 96 (90) | 92 (86) |
| 2 | 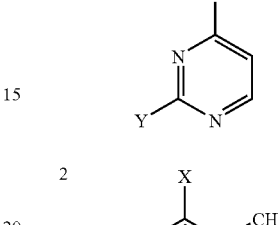 | 96 (91) | 95 (91) | 91 (85) |
| 3 | 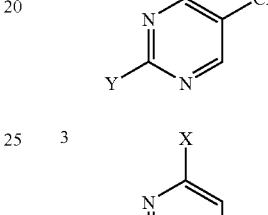 | 96 (91) | 90 (90) | 90 (86) |
| 4 | 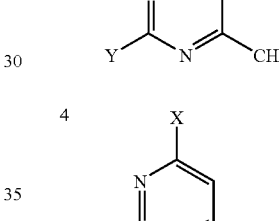 | 93 (89) | 95 (90) | 96 (88) |
| 5 | 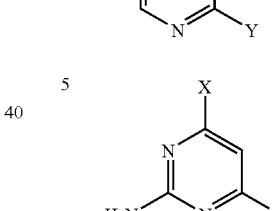 | 91 (85) | 88 (82) | 90 (83) |
| 6 | 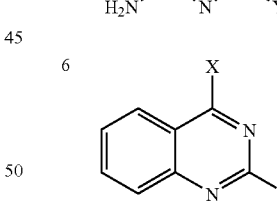 | 96 (90) | 94 (89) | 93 (89) |
| 7 | 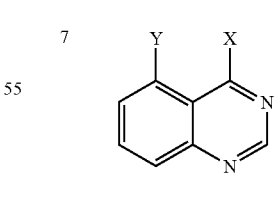 | 80 (79) | 89 (78) | 85 (78) |
| 8 | 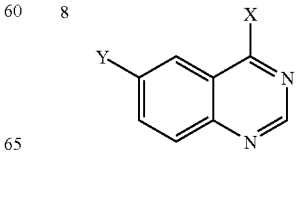 | 92 (85) | 93 (86) | 94 (85) |

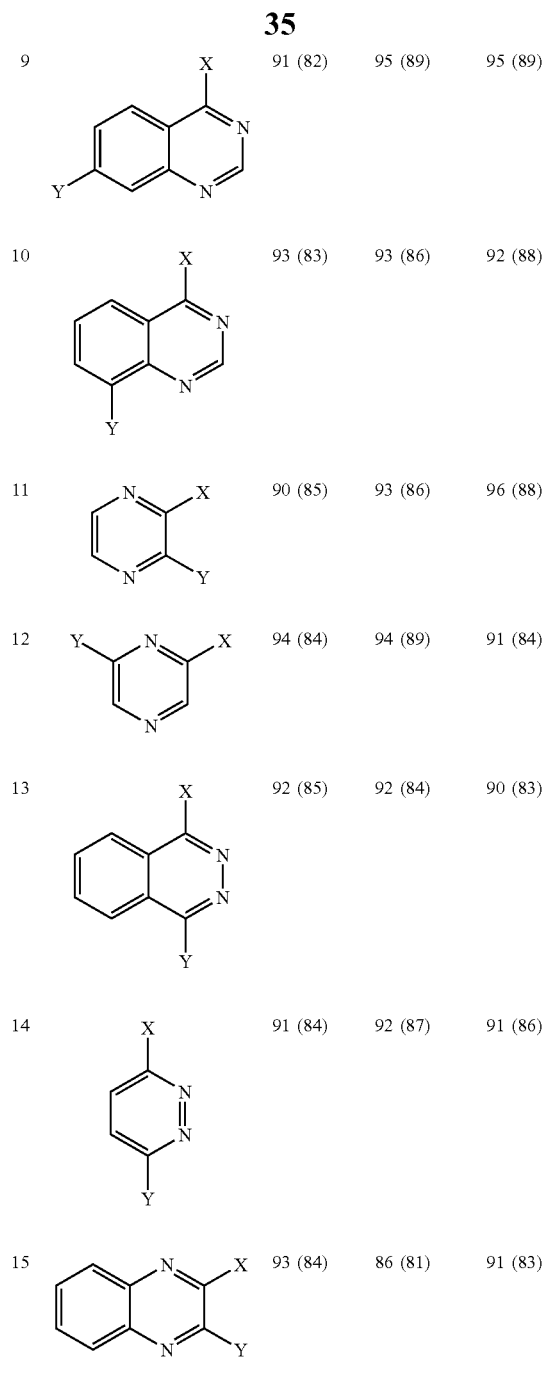

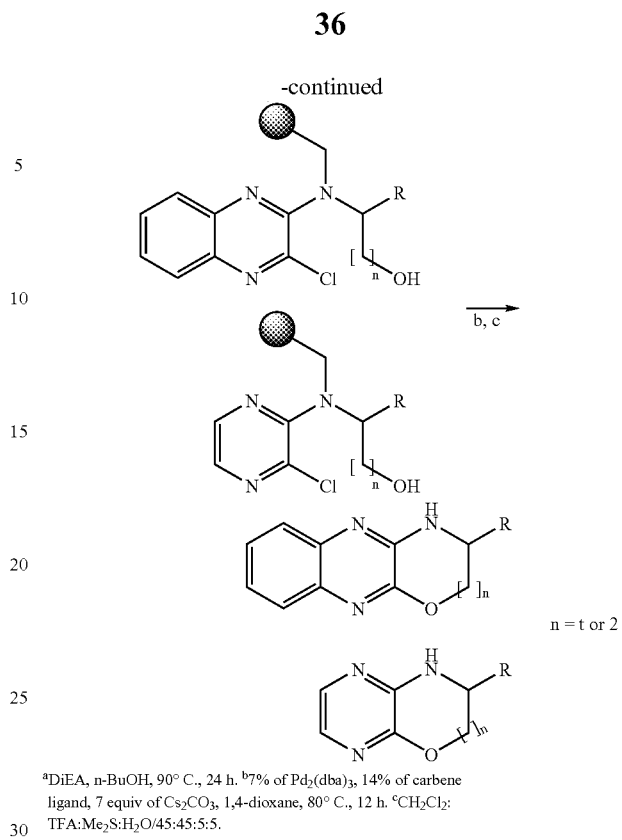

$n = 1$ or 2

[a]DiEA, n-BuOH, 90° C., 24 h. [b]7% of Pd$_2$(dba)$_3$, 14% of carbene ligand, 7 equiv of Cs$_2$CO$_3$, 1,4-dioxane, 80° C., 12 h. [c]CH$_2$Cl$_2$: TFA:Me$_2$S:H$_2$O/45:45:5:5.

In summary, in this aspect, the invention provides a general method for the solid phase synthesis of various substituted heterocycles. Alkylated purines halogenated at the 2,6, 6,8 or 2,6,8 positions and various dihaloheterocycles can be captured onto solid support and further elaborated by aromatic substitution with amines at elevated temperature or by anilines, boronic acids, and phenols via palladium-catalyzed cross-coupling reactions.

The combinatorial scaffold approach described herein can be used in conjunction with one or more of the methods for making substituted heterocycles (including purines) that are described in U.S. Provisional Application No. 60/328,763, which is entitled "Expanding the Diversity of Purine Libraries," and was filed on Oct. 12, 2001. The approach is also suitable for use with the methods for making substituted heterocycles described in U.S. Provisional Application No. 60/328,741, which is entitled "A Concise and Traceless Linker Strategy Toward Combinatorial Libraries of 2,6,9-Substituted Purines," and was filed on Oct. 12, 2001, and in U.S. Provisional Application Nos. 60/346,552 and 60/347,037, entitled "Methods For the Synthesis of Substituted Purine Libraries," which were filed on Jan. 7 and 8, 2002.

Pharmaceutical Formulations

In another preferred embodiment, the present invention provides a pharmaceutical formulation comprising a compound of the invention and a pharmaceutically acceptable carrier.

The compounds described herein, or pharmaceutically acceptable addition salts or hydrates thereof, can be delivered to a patient using a wide variety of routes or modes of administration. Suitable routes of administration include, but are not limited to, inhalation, transdermal, oral, rectal, Scheme 3

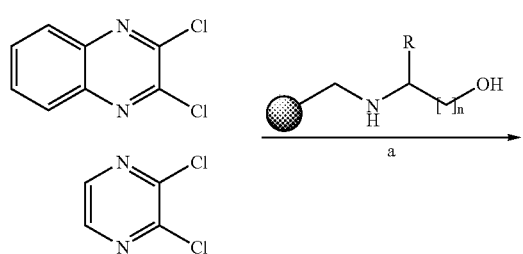

transmucosal, intestinal and parenteral administration, including intramuscular, subcutaneous and intravenous injections.

The compounds described herein, or pharmaceutically acceptable salts and/or hydrates thereof, can be administered singly, in combination with other compounds of the invention, and/or in cocktails combined with other therapeutic agents. Of course, the choice of therapeutic agents that can be co-administered with the compounds of the invention will depend, in part, on the condition being treated.

For example, when administered to a patient undergoing cancer treatment, the compounds can be administered in cocktails containing anti-cancer agents and/or supplementary potentiating agents. The compounds can also be administered in cocktails containing agents that treat the side-effects of radiation therapy, such as anti-emetics, radiation protectants, etc.

Supplementary potentiating agents that can be co-administered with the compounds of the invention include, e.g., tricyclic anti-depressant drugs (e.g., imipramine, desipramine, amitriptyline, clomipramine, trimipramine, doxepin, nortriptyline, protriptyline, amoxapine and maprotiline); non-tricyclic and anti-depressant drugs (e.g., sertraline, trazodone and citalopram); $Ca^{+2}$ antagonists (e.g., verapamil, nifedipine, nitrendipine and caroverine); amphotericin; triparanol analogues (e.g., tamoxifen); anti-arrhythmic drugs (e.g., quinidine); antihypertensive drugs (e.g., reserpine); thiol depleters (e.g., buthionine and sulfoximine); and calcium leucovorin.

The active compound(s) of the invention are administered per se or in the form of a pharmaceutical composition wherein the active compound(s) is in admixture with one or more pharmaceutically acceptable carriers, excipients or diluents. Pharmaceutical compositions for use in accordance with the present invention are typically formulated in a conventional manner using one or more physiologically acceptable carriers comprising excipients and auxiliaries, which facilitate processing of the active compounds into preparations which, can be used pharmaceutically. Proper formulation is dependent upon the route of administration chosen.

For injection, the agents of the invention can be formulated in aqueous solutions, preferably in physiologically compatible buffers such as Hanks's solution, Ringer's solution, or physiological saline buffer. For transmucosal administration, penetrants appropriate to the barrier to be permeated are used in the formulation. Such penetrants are generally known in the art.

For oral administration, the compounds can be formulated readily by combining the active compound(s) with pharmaceutically acceptable carriers well known in the art. Such carriers enable the compounds of the invention to be formulated as tablets, pills, dragees, capsules, liquids, gels, syrups, slurries, suspensions and the like, for oral ingestion by a patient to be treated. Pharmaceutical preparations for oral use can be obtained solid excipient, optionally grinding a resulting mixture, and processing the mixture of granules, after adding suitable auxiliaries, if desired to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxyniethylcellulose, and/or polyvinylpyrrolidone (PVP). If desired, disintegrating agents can be added, such as the cross-linked polyvinyl pyrrolidone, agar, or alginic acid or a salt thereof such as sodium alginate.

Dragee cores are provided with suitable coatings. For this purpose, concentrated sugar solutions can be used, which can optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments can be added to the tablets or dragee coatings for identification or to characterize different combinations of active compound doses.

Pharmaceutical preparations, which can be used orally, include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds can be dissolved or suspended in suitable liquids, such as fatty oils, liquid paraffin, or liquid polyethylene glycols. In addition, stabilizers can be added. All formulations for oral administration should be in dosages suitable for such administration.

For buccal administration, the compositions may take the form of tablets or lozenges formulated in conventional manner.

For administration by inhalation, the compounds for use according to the present invention are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g., gelatin for use in an inhaler or insufflator may be formulated containing a powder mix of the compound and a suitable powder base such as lactose or starch.

The compounds may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents may be added, such as the cross-linked polyvinyl pyrrolidone, agar, or alginic acid or a salt thereof such as sodium alginate.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances, which increase the viscosity of the suspension, such as sodium carboxymethyl cellulose, sorbitol, or dextran. Optionally, the suspension may also contain suitable stabilizers or agents, which increase the solubility of the compounds to allow for the preparation of highly, concentrated solutions.

Alternatively, the active ingredient may be in powder form for constitution with a suitable vehicle, e.g., sterile pyrogen-free water, before use.

The compounds may also be formulated in rectal compositions such as suppositories or retention enemas, e.g., containing conventional suppository bases such as cocoa butter or other glycerides.

In addition to the formulations described previously, the compounds may also be formulated as a depot preparation. Such long acting formulations may be administered by implantation or transcutaneous delivery (e.g., subcutaneously or intramuscularly), intramuscular injection or a transdermal patch. Thus, for example, the compounds may be formulated with suitable polymeric or hydrophobic materials (e.g., as an emulsion in an acceptable oil) or ion exchange resins, or as sparingly soluble derivatives, for example, as a sparingly soluble salt.

The pharmaceutical compositions also may comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols.

EXAMPLES

General Considerations. Purity of compounds were assessed by reverse-phase liquid chromatography—mass spectrometer (Agilent Series 1100 LC—MS) with an UV detector at $\lambda=255$ nm (reference at 360 mn) and an API-ES ionization source. NMR spectra were recorded on Bruker-400 MHz and 500 MHz instrument and calibrated using residual undeuterated solvent as an internal reference. The following abbreviations were used to designate the multiplicities: s=singlet, d=doublet, t=triplet, q=quartet, m=multiplet. LC elution methods (using a Phenomenex Luna 50*2.00 mm 5 µ C18 column): (1) 10 minutes method: starting from 5% solvent A (acetonitrile) in solvent B (water with 0.5% acetic acid) and running the gradient to 95% A in 8 minutes, followed by 2 minutes elution with 95% A. (2) 17 minutes method: starting from 5% solvent A (acetonitrile) in solvent B (water with 0.5% acetic acid) and running the gradient to 95% A in 15 minutes, followed by 2 minutes elution with 95% A.

Example 1

General Procedure for the Solution Phase Synthesis of 2,6,9-substituted Purines

Boronic Acid coupling reactions: A 10 mL flame-dried Schlenk flask equipped with a magnetic stir bar was charged with 2-chloro-6-(4-methoxybenzylamino)-9-isopropylpurine (0.193 g, 0.5 mmol, 1.0 equiv), 2,4-dimethoxyphenylboronic acid (0.136 g, 0.75 mmol, 1.5 equiv), $Pd_2(dba)_3$ (0.0069 g, 0.0075 mmol, 0.015 equiv.), ligand 1 (0.0051 g, 0.015 mmol, 0.03 equiv.) and $Cs_2CO_3$ (0.326 g, 1.0 mmol, 2.0 equiv.). The Schlenk flask was evacuated and backfilled with argon and charged with anhydrous 1,4-dioxane (2.0 mL). The reaction was stirred under argon at 80° C. and monitored by TLC. When the reaction was complete after 8 hours, the solvent was removed in vacuo and the reaction crude was purified by flash column chromatography (3% methanol in dichloromethane) to afford desired 2-(2,4-dimethoxyphenyl)-6-(4-methoxybenzylamino)-9-isopropylpurine (207 mg, 96%). $^1$H NMR (400 MHz, $CDCl_3$) δ 1.59 (d, 6H, J=6.8 Hz), 3.79 (s, 3H), 3.84 (s, 3H), 3.85 (s, 3H), 4.87–4.96 (m, 3H), 6.14 (br, 1H), 6.57–6.60 (m, 2H), 6.85 (d, 2H, J=8.6 Hz), 7.34 (d, 2H, J=8.6 Hz), 7.73 (s, 1H), 7.78 (d, 1H, J=8.2 Hz); HRMS (MALDI-FTMS) $[MH^+]$ $C_{24}H_{28}N_5O_3$ 434.2187, found: 434.2168.

Aniline coupling: A 10 mL flame-dried Schlenk flask equipped with a magnetic stir bar was charged with 2-chloro-6-(4-methoxybenzylamino)-9-isopropylpurine (0.193 g, 0.5 mmol, 1.0 equiv), 4-methoxyaniline (0.092 g, 0.75 mmol, 1.5 equiv), $Pd_2(dba)_3$ (0.0069 g, 0.0075 mmol, 0.015 equiv.), ligand 1 (0.0051 g, 0.015 mmol, 0.03 equiv.) and KO$^t$Bu (0.112 g, 1.0 mmol, 2.0 equiv.). The Schlenk flask was evacuated and backfilled with argon and charged with anhydrous 1,4-dioxane (2.0 mL). The reaction was stirred under argon at 80° C. and monitored by TLC. When the reaction was complete after 8 hours, the solvent was removed in vacuo and the reaction crude was purified by flash column chromatography (3% methanol in dichloromethane) to afford desired 2-(4-methoxyphenylamino)-6-(4-methoxybenzylamino)-9-isopropylpurine (203 mg, 97%): $^1$H NMR (500 MHz, $CDCl_3$) δ 1.54 (d, 6H, J=6.6 Hz), 3.76 (s, 3H), 3.78 (s, 3H), 4.66 (m, 1H, J=6.6 Hz), 4.72 (br, 2H), 6.06 (br, 1H), 6.60 (br, 1H), 6.82 (d, 2H, J=13 Hz), 6.84 (d, 2H, J=13 Hz), 7.09 (s, 1H), 7.26 (d, 2H, J=8.8 Hz), 7.42 (s, 1H), 7.56 (d, 2H, J=8.8 Hz); HRMS (MALDI-FTMS) $[MH^+]$ $C_{23}H_{27}N_6O_2$ 419.2195, found: 419.2209.

Phenol coupling: A 10 mL flame-dried Schlenk flask equipped with a magnetic stir bar was charged with 2-chloro-6-(4-methoxybenzylamino)-9-isopropylpurine (0.193 g, 0.5 mmol, 1.0 equiv), 4-methylphenol (0.081 g, 0.75 mmol, 1.5 equiv), $Pd_2(dba)_3$ (0.0069 g, 0.0075 mmol, 0.015 equiv.), ligand 1 (0.0051 g, 0.015 mmol, 0.03 equiv.) and KO$^t$Bu (0.112 g, 1.0 mmol, 2.0 equiv.). The Schlenk flask was evacuated and backfilled with argon and charged with anhydrous 1,4-dioxane (2.0 mL). The reaction was stirred under argon at 90° C. and monitored by TLC. When the reaction was complete after 8 hours, the solvent was removed in vacuo and the reaction crude was purified by flash column chromatography (2% methanol in dichloromethane) to afford desired 2-(4-methylphenoxy)-6-(4- methoxy-benzylamino)-9-isopropylpurine (180 mg, 90%): $^1$H NMR (400 MHz, CDCl$_3$) δ 1.53 (d, 6H, J=6.8 Hz), 2.37 (s, 3H), 3.79 (s, 3H), 4.54 (br, 2H), 4.71 (m, 1H, J=6.8 Hz), 6.35 (br, 1H), 6.81 (d, 2H, J=8.4 Hz), 7.10–7.18 (m, 6H), 7.65 (s, 1H); HRMS (MALDI-FTMS) [MH$^+$] C$_{23}$H$_{26}$N$_5$O$_2$ 404.2081, found: 404.2080.

Purine N9 arylation via boronic acids/cupric acetate: A 20 mL glass vial equipped with a magnetic stir bar was charged with 2,6-dichloropurine (0.200 g, 1.06 mmol, 1.0 equiv), 4-methylphenylboronic acid (0.288 g, 2.12 mmol, 2.0 equiv), anhydrous cupric acetate (0.384 g, 2.12 mmol, 2.0 equiv.), 4 Å activated molecular sieves (0.500 g), triethylamine (0.443 mL, 3.18 mmol, 3.0 equiv.) and dichloromethane (5.0 mL). The reaction was stirred under air at ambient temperature and monitored by TLC. When the reaction was complete after 24 hours, it was filtered through Celite, washed with methanol and purified by flash column chromatography (1% methanol in dichloromethane) to afford desired 2,6-dichloro-9-(4-methylphenyl)-purine (0.136 g, 47%). $^1$H NMR (400 MHz, CDCl$_3$) δ 2.47 (s, 3H), 7.41 (d, 2H, J=8.1 Hz), 7.54 (d, 2H, J=8.1 Hz), 8.35 (s, 1H); HRMS (MALDI-FTMS) C$_{12}$H$_8$Cl$_2$N$_4$ [MH$^+$] 279.0199, found: 279.0208.

Example 2

General Procedure for Combinatorial Synthesis of Heterocycle Libraries.

Reductive Amination for Synthesis of PAL-resin-bound amine (1). To a suspension of 4-formyl-3,5-dimethoxyphenoxymethyl functionalized polystyrene resin (PAL) (10.0 g, 11.3 mmol) in DMF (350 mL) was added a primary amine (56.5 mmol), followed by addition of sodium triacetoxyborohydride (7.18 g, 33.9 mmol) and acetic acid (6.52 mL, 113 mmol). The mixture was shaken gently at room temperature. After overnight the resin 1 was washed by methanol (300 mL×4) and dichloromethane (300 mL×4) and dried under vacuum. The complete conversion of PAL aldehyde to resin-bound amine was confirmed by disappearance of the aldehyde stretch.

Resin Capture of Dichloroheterocycles (C). To a solution of dichloro-heterocycle (S) (15.0 mmol) in n-butanol (200 mL) was added PAL-resin-bound amine 1 (10.0 mmol), followed by addition of diisopropylethylamine (5.2 mL, 30.0 mmol). The suspension was heated to 90° C. under argon. After 12 hours, the resin was washed by methanol (200 mL×4) and dichloromethane (200 mL×4) and dried under vacuum. The complete conversion of secondary amine (PAL-amine) to tertiary amine was confirmed by bromophenol blue test.

Substitution of Remaining Chloro Group with Boronic Acids via Suzuki Coupling and Product Cleavage (P1). A 10 mL flame-dried Schlenk flask was charged with resin C (0.10 mmol, 1.0 equiv), arylboronic acid (0.50 mmol, 5.0 equiv), Pd$_2$(dba)$_3$ (0.007 mmol, 0.07 equiv.), carbine ligand (0.014 mmol, 0.14 equiv.) and Cs$_2$CO$_3$ (0.60 mmol, 6.0 equiv.). The Schlenk flask was evacuated and backfilled with argon and charged with anhydrous 1,4-dioxane (1.0 mL). The reaction was heated to 80° C. under argon. After 12 hours, the resin was washed by sodium diethyldithiocarbamate solution (0.05M in DMF, 1 mL×4), dichloromethane (1 mL×4) and methanol (1 mL×4) and dried under vacuum. The derivatized resin was subsequently cleaved in CH$_2$Cl$_2$:TFA:Me$_2$S:H$_2$O/45:45:5:5/v:v:v:v (0.5 mL) for two hours. The solution was collected and the solvent was removed in vacuo to afford desired final product (P1).

Substitution of Remaining Chloro Group with Anilines or Amines via Palladium-Catalyzed Reaction and Product Cleavage (P2). A 10 mL flame-dried Schlenk flask was charged with resin C (0.10 mmol, 1.0 equiv), aniline or amine (0.50 mmol, 5.0 equiv), Pd$_2$(dba)$_3$ (0.007 mmol, 0.07 equiv.), carbine ligand (0.014 mmol, 0.14 equiv.) and KO$^t$Bu (0.60 mmol, 6.0 equiv.). The Schlenk flask was evacuated and backfilled with argon and charged with anhydrous 1,4-dioxane (1.0 mL). The reaction was heated to 80° C. under argon. After 12 hours, the resin was washed by sodium diethyldithiocarbamate solution (0.05M in DMF, 1 mL×4), dichloromethane (1 mL×4) and methanol (1 mL×4) and dried under vacuum. The derivatized resin was subsequently cleaved in CH$_2$Cl$_2$:TFA:Me$_2$S:H$_2$O/45:45:5:5/v:v:v:v (0.5 mL) for two hours. The solution was collected and the solvent was removed in vacuo to afford desired final product (P2).

Substitution of Remaining Chloro Group with Phenols via Palladium-Catalyzed Reaction and Product Cleavage (P3). A 10 mL flame-dried Schlenk flask was charged with resin C (0.10 mmol, 1.0 equiv), phenol (0.50 mmol, 5.0 equiv), Pd$_2$(dba)$_3$ (0.007 mmol, 0.07 equiv.), phosphine ligand (0.028 mmol, 0.28equiv.) and K$_3$PO$_4$ (0.70 mmol, 7.0 equiv.). The Schlenk flask was evacuated and backfilled with argon and charged with anhydrous toluene (1.0 mL). The reaction was heated to 80° C. under argon. After 12 hours, the derivatized resin was washed by sodium diethyldithiocarbamate solution (0.05M in DMF, 1 mL×4), dichloromethane (1 mL×4) and methanol (1 mL×4) and dried under vacuum. The resin was subsequently cleaved in CH$_2$Cl$_2$:TFA:Me$_2$S:H$_2$O/45:45:5:5/v:v:v:v (0.5 mL) for two hours. The solution was collected and the solvent was removed in vacuo to afford desired final product (P3).

Substitution of Remaining Chloro Group with Amines via non-Palladium-Catalyzed Amination Reaction without Base and Product Cleavage (P4). The resin C (0.05 mmol) was suspended in the solution of an amine (2M in n-butanol, 0.2 mL). After 12 hours heating at 80° C. in a sealed reaction vessel under argon, the resin was washed with methanol (1 mL×4) and dichloromethane (1 mL×4) and dried under vacuum. It was subsequently cleaved using CH$_2$Cl$_2$:TFA: Me$_2$S:H$_2$O/45:45:5:5/v:v:v:v (0.3 mL) to afford desired final product (P4) (>90% HPLC purity in average, 80% purified yield).

Substitution of Remaining Chloro Group with Amines via non-Palladium-Catalyzed Amination Reaction with KO$^t$Bu as Base and Product Cleavage. To a suspension of resin C (0.05 mmol) in THF (anhydrous, 0.25 mL) was added an amine (0.25 mmol), followed by addition of KO$^t$Bu solution (in THF, 1.0M, 0.25 mL, 0.25 mmol). After 12 hours heating at 70° C. in a sealed reaction vessel under argon, the resin was washed with methanol (1 mL×4) and dichloromethane (1 mL×4) and dried under vacuum. It was subsequently cleaved using CH$_2$Cl$_2$:TFA:Me$_2$S:H$_2$O/45:45:5:5/v:v:v:v (0.3 mL) to afford desired final product (in average >85% HPLC purity, 80% purified yield).

TABLE 1

Validation of palladium catalyzed cross-coupling reactions for derivatizing resin-bound 2-chloro-6-aminopurine with boronic acids, anilines, amines and phenols. (Purities refer to HPLC purities, and yields refer to isolated yields by preparative TLC.)

| Entry | C2 Substituents via boronic acids | Retention Time (min) | Calculated [M] | Observed [MH+] | Purity & Yields (%) | Entry | C2 Substituents via anilines | Retention Time (min) | Calculated [M] | Observed [MH+] | Purity & Yields (%) |
|---|---|---|---|---|---|---|---|---|---|---|---|
| B1 | 4-F-C6H4 | 8.28 | 391.18 | 392.20 | 90 (84) | An1 | 4-OCH3-C6H4-NH | 5.77[a] | 418.21 | 419.20 | 97 (90) |
| B2 | 2-OCH3-C6H4 | 5.72 | 403.20 | 404.20 | 94 (85) | An2 | benzodioxane-NH | 6.59 | 446.21 | 447.20 | 96 (91) |
| B3 | 2,4-(OCH3)2-C6H3 | 5.28 | 433.21 | 434.20 | 92 (85) | An3 | 2,6-(CH3)2-4-CH3-C6H2-NH | 6.83 | 430.25 | 431.20 | 89 (81) |

TABLE 1-continued

Validation of palladium catalyzed cross-coupling reactions for derivatizing resin-bound 2-chloro-6-aminopurine with boronic acids, anilines, amines and phenols. (Purities refer to HPLC purities, and yields refer to isolated yields by preparative TLC.)

| Entry | C2 Substituents via amines | Retention Time (min) | Calculated [M] | Observed [MH+] | Purity & Yields (%) | Entry | C2 Substituents via amines | Retention Time (min) | Calculated [M] | Observed [MH+] | Purity & Yields (%) |
|---|---|---|---|---|---|---|---|---|---|---|---|
| B4 | benzofuran-2-yl | 8.02 | 413.19 | 414.20 | 91 (82) | An4 | 2-fluoroanilino | 7.54 | 406.19 | 407.20 | 89 (80) |
| B5 | 4-acetylphenyl | 7.57 | 415.20 | 416.20 | 90 (80) | An5 | indan-5-ylamino | 7.82 | 428.23 | 429.20 | 95 (88) |
| B6 | biphenyl-3-yl | 9.05 | 449.22 | 450.20 | 90 (85) | An6 | N-methylanilino | 7.63 | 402.22 | 403.20 | 97 (91) |

| Entry | C2 Substituents via amines | Retention Time (min) | Calculated [M] | Observed [MH+] | Purity & Yields (%) | Entry | C2 Substituents via phenols | Retention Time (min) | Calculated [M] | Observed [MH+] | Purity & Yields (%) |
|---|---|---|---|---|---|---|---|---|---|---|---|
| Am1 | valinol | 3.98 | 396.24 | 399.20 | 89 (83) | P1 | 2-methylphenoxy | 7.43 | 403.20 | 404.20 | 90 (82) |

R group in core structure: 4-methoxybenzylamino-9-isopropyl-9H-purine

TABLE 1-continued
Validation of palladium catalyzed cross-coupling reactions for derivatizing resin-bound 2-chloro-6-aminopurine with boronic acids, anilines, amines and phenols. (Purities refer to HPLC purities, and yields refer to isolated yields by preparative TLC.)
| | | | | | | | | | |
|---|---|---|---|---|---|---|---|---|---|
| Am2 | 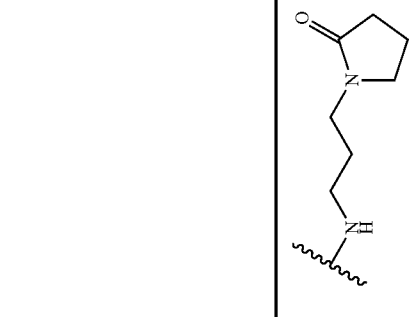 | 4.31 | 437.25 | 438.30 | 97 (90) | P2 | 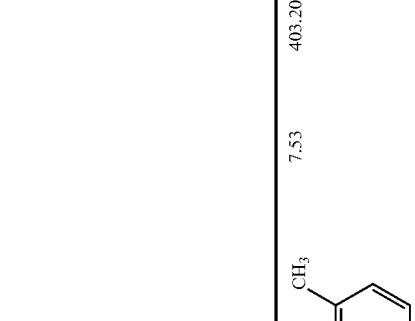 | 7.53 | 403.20 | 404.20 | 91 (82) |
| Am3 | 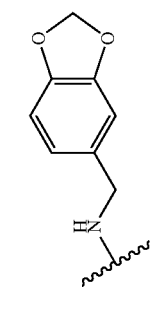 | 5.81 | 446.21 | 447.20 | 96 (91) | P3 |  | 7.52 | 403.20 | 404.20 | 92 (81) |
| Am4 | | 5.07 | 431.24 | 432.20 | 91 (84) | P4 | 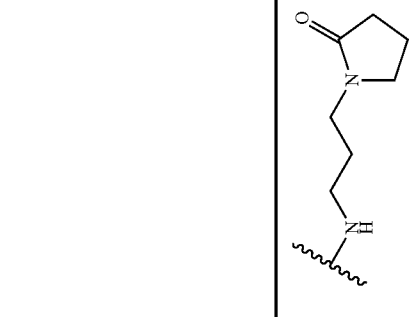 | 7.59 | 439.20 | 440.20 | 90 (80) |
| Am5 | | 5.38 | 396.23 | 397.20 | 92 (84) | P5 |  | 7.30 | 407.18 | 408.20 | 88 (81) |

TABLE 1-continued
Validation of palladium catalyzed cross-coupling reactions for derivatizing resin-bound 2-chloro-6-aminopurine with boronic acids, anilines, amines and phenols. (Purities refer to HPLC purities, and yields refer to isolated yields by preparative TLC.)
| Am6 | 8 71 | 525 25 | 526.20 | 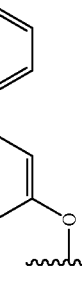 | 98 (90) | P6 |  | 8.03 | 465 22 | 466 20 | 92 (80) |
[a] Using 17 minutes LC/MS method.

TABLE 2

Validation of resin-bound chloroheterocyclic scaffolds which can be derivatized via Suzuki coupling reaction. (Purities refer to HPLC purities, and yields refer to isolated yields by preparative TLC.)

| Entry | Scaffolds (R2) | Retention Time (min) | Calculated [M] | Observed [MH+] | Purity & Yield (%) |
|---|---|---|---|---|---|
| 1 | pyrimidine | 4.46 | 321.15 | 322.20 | 95 (90) |
| 2 | 5-methylpyrimidine | 4.47 | 335.16 | 336.20 | 95 (91) |
| 3 | 6-methylpyrimidine | 4.31 | 335.16 | 336.20 | 96 (91) |
| 4 | pyrimidine isomer | 4.72 | 321.15 | 322.20 | 93 (89) |
| 5 | 2-aminopyrimidine | 4.11 | 336.16 | 337.15 | 91 (85) |
| 6 | quinazoline | 4.91 | 371.16 | 372.20 | 95 (90) |
| 7 | quinazoline isomer | 4.87 | 371.16 | 372.20 | 86 (79) |
| 8 | quinazoline isomer | 4.80 | 371.16 | 372.20 | 92 (85) |
| 9 | quinazoline isomer | 4.65 | 371.16 | 372.20 | 91 (82) |
| 10 | quinazoline isomer | 4.60 | 371.16 | 372.20 | 93 (83) |
| 11 | pyrazine | 6.81 | 321.15 | 322.10 | 95 (85) |
| 12 | pyrazine isomer | 7.01 | 321.15 | 322.20 | 94 (84) |
| 13 | phthalazine | 4.51 | 371.16 | 372.10 | 92 (85) |
| 14 | pyridazine | 4.69 | 321.15 | 322.10 | 91 (84) |

TABLE 2-continued

Validation of resin-bound chloroheterocyclic scaffolds which can be derivatized via Suzuki coupling reaction. (Purities refer to HPLC purities, and yields refer to isolated yields by preparative TLC.)

| Entry | Scaffolds (R2) | Retention Time (min) | Calculated [M] | Observed [MH+] | Purity & Yield (%) |
|---|---|---|---|---|---|
| 15 | quinoxaline | 7.94 | 371.16 | 372.15 | 93 (84) |
| 16 | 9-isopropyl purine | 7.53[a] | 403.20 | 404.30 | 89 (80) |

[a]Using 17 minutes LC/MS method.

TABLE 3

Validation of resin-bound chloroheterocyclic scaffolds which can be derivatized via palladium catalyzed amination reaction. (Purities refer to HPLC purities, and yields refer to isolated yields by preparative TLC.)

| Entry | Scaffolds (R2) | Retention Time (min) | Calculated [M] | Observed [MH+] | Purity & Yield (%) |
|---|---|---|---|---|---|
| 1 | pyrimidine (2,4) | 4.26 | 336.16 | 337.15 | 96 (90) |
| 2 | 5-methylpyrimidine | 4.32 | 350.17 | 351.20 | 95 (91) |
| 3 | 6-methylpyrimidine | 4.26 | 350.17 | 351.20 | 96 (90) |
| 4 | pyrimidine (4,6) | 4.25 | 336.16 | 337.20 | 95 (90) |
| 5 | 2-aminopyrimidine | 4.18 | 351.17 | 352.20 | 88 (82) |
| 6 | quinazoline (2,4) | 4.58 | 386.17 | 387.20 | 94 (89) |
| 7 | quinazoline (4,5) | 4.59 | 386.17 | 387.20 | 89 (78) |
| 8 | quinazoline (4,6) | 4.58 | 386.17 | 387.20 | 93 (86) |
| 9 | quinazoline (4,7) | 4.65 | 386.17 | 387.20 | 95 (89) |

TABLE 3-continued

Validation of resin-bound chloroheterocyclic scaffolds which can be derivatized via palladium catalyzed amination reaction. (Purities refer to HPLC purities, and yields refer to isolated yields by preparative TLC.)

| Entry | Scaffolds (R2) | Retention Time (min) | Calculated [M] | Observed [MH+] | Purity & Yield (%) |
|---|---|---|---|---|---|
| 10 | (quinazoline) | 6.13 | 386.17 | 387.20 | 93 (85) |
| 11 | (pyrazine) | 5.98 | 336.16 | 337.10 | 93 (86) |
| 12 | (pyrimidine) | 5.72 | 336.16 | 337.10 | 94 (89) |
| 13 | (phthalazine) | 4.38 | 386.16 | 387.20 | 92 (84) |
| 14 | (pyridazine) | 4.12 | 336.16 | 337.10 | 92 (87) |
| 15 | (quinoxaline) | 7.61 | 386.17 | 387.20 | 88 (81) |
| 16 | (purine, isopropyl) | 5.77[a] | 418.21 | 419.30 | 91 (85) |

[a]Using 17 minutes LC/MS method.

Table 4. Validation of resin-bound chloroheterocyclic scaffolds which can be derivatized via palladium catalyzed C—O bond formation reaction. (Purities refer to HPLC purities, and yields refer to isolated yields by preparative TLC.)

TABLE 4

Validation of resin-bound chloroheterocyclic scaffolds which can be derivatized via palladium catalyzed C—O bond formation reaction. (Purities refer to HPLC purities, and yields refer to isolated yields by preparative TLC.)

| Entry | Scaffolds (R2) | Retention Time (min) | Calculated [M] | Observed [MH+] | Purity & Yield (%) |
|---|---|---|---|---|---|
| 1 | (pyrimidine) | 4.73 | 337.14 | 338.10 | 92 (86) |
| 2 | (5-methylpyrimidine) | 4.68 | 351.16 | 352.20 | 91 (85) |
| 3 | (6-methylpyrimidine) | 4.59 | 351.16 | 352.20 | 93 (88) |
| 4 | (pyrimidine) | 6.30 | 337.14 | 338.10 | 96 (88) |
| 5 | (2-aminopyrimidine) | 4.79 | 352.15 | 353.10 | 90 (83) |
| 6 | (quinazoline) | 4.99 | 387.16 | 388.10 | 93 (89) |

TABLE 4-continued

Validation of resin-bound chloroheterocyclic scaffolds which can be derivatized via palladium catalyzed C—O bond formation reaction. (Purities refer to HPLC purities, and yields refer to isolated yields by preparative TLC.)

| Entry | Scaffolds (R2) | Retention Time (min) | Calculated [M] | Observed [MH+] | Purity & Yield (%) |
|---|---|---|---|---|---|
| 7 | | 4.56 | 387.16 | 388.20 | 85 (78) |
| 8 | | 4.83 | 387.16 | 388.15 | 94 (85) |
| 9 | | 4.70 | 387.16 | 388.10 | 95 (89) |
| 10 | | 4.36 | 387.16 | 388.15 | 92 (88) |
| 11 | | 7.16 | 337.14 | 338.10 | 96 (88) |
| 12 | | 6.90 | 337.14 | 338.10 | 91 (84) |
| 13 | | 4.76 | 387.16 | 388.10 | 90 (83) |
| 14 | | 4.64 | 336.16 | 337.10 | 91 (86) |
| 15 | | 8.15 | 337.14 | 338.10 | 91 (83) |
| 16 | | 6.72[a] | 419.20 | 420.30 | 90 (85) |

[a]Using 17 minutes LC/MS method.

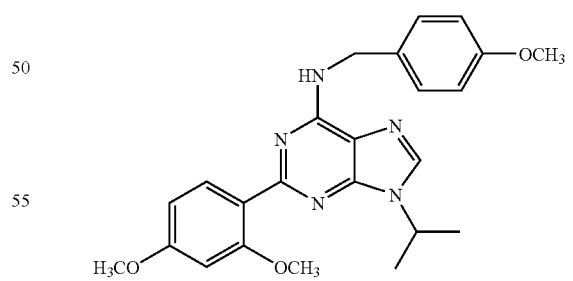

2-(2,4-dimethoxyphenyl)-6-(4-methoxybenzylamino)-9-isopropylpurine. $^1$H NMR (400 MHz, CDCl$_3$) δ 1.59 (d, 6H, J=6.8 Hz), 3.79 (s,3H), 3.84 (s, 3H), 3.85 (s, 3H), 4.87–4.96 (m, 3H), 6.14 (br, 1H), 6.57–6.60 (m, 2H), 6.85 (d, 2H), J=8.6 Hz), 7.34 (d, 2H, J=8.6 Hz), 7.73 (s, 1H), 7.78 (d, 1H, J=8.2 Hz); HRMS (MALDI-FTMS) [MH+] C$_{24}$H$_{28}$N$_5$O$_3$ 434.2187, found: 434.2168

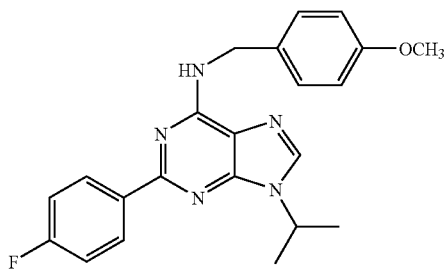

2-(4-fluorophenyl)-6-(4-methoxybenzylamino)-9-isopropylpurine. $^1$H NMR (400 MHz, CDCl$_3$) δ 1.61 (d, 6H, J=6.8 Hz), 3.81 (s, 3H), 4.87 (br, 2H), 5.04 (m, 1H, J=6.8 Hz), 6.85 (d, 2H, J=8.4 Hz), 7.00 (d, 2H, J=8.8 Hz), 7.17 (d, 2H, J=8.4 Hz), 7.73 (d, 2H, J=8.8 Hz), 8.38 (s, 1H); HRMS (MALDI-FTMS) [MH$^+$] C$_{22}$H$_{23}$FN$_5$O 392.1881, found: 392.1885

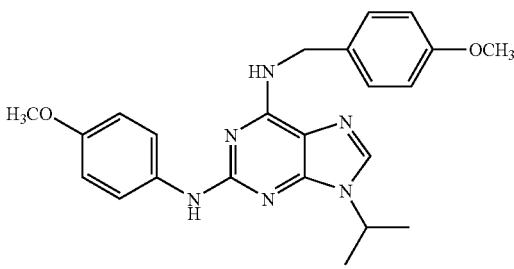

2-(4-methoxyphenylamino)-6-(4-methoxybenzylamino)-9-isopropylpurine: $^1$H NMR (500 MHz, CDCl$_3$) δ 1.54 (d, 6H, J=6.6 Hz), 3.76 (s, 3H), 3.78 (s, 3H), 4.66 (m, 1H, J=6.6 Hz), 4.72 (br, 2H), 6.06 (br, 1H), 6.60 (br, 1H), 6.82 (d, 2H, J=13 Hz), 6.84 (d, 2H, J=13 Hz), 7.09 (s, 1H), 7.26 (d, 2H, J=8.8 Hz), 7.42 (s, 1H), 7.56 (d, 2H, J=8.8 Hz); HRMS (MALDI-FTMS) [MH$^+$] C$_{23}$H$_{27}$N$_6$O$_2$ 419.2195, found: 419.2209

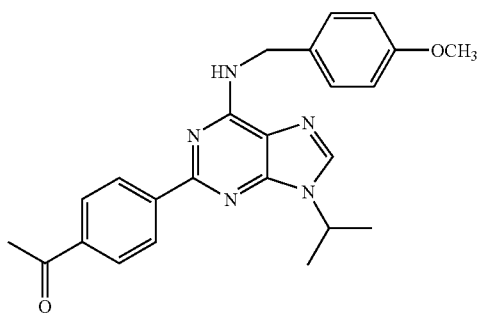

2-(4-acetylphenyl)-6-(4-methoxybenzylamino)-9-isopropylpurine. $^1$H NMR (400 MHz, CDCl$_3$) δ 1.79 (d, 6H, J=6.8 Hz), 2.52 (s, 3H), 3.81 (s, 3H), 4.91 (d, 2H), 5.13 (m, 1H, J=6.8 Hz), 6.82 (d, 2H, J=8.5 Hz), 7.15 (d, 2H, J=8.5 Hz), 7.88 (d, 2H, J=8.1 Hz), 7.97 (d, 2H, J=8.1 Hz), 8.65 (s, 1H); HRMS (MALDI-FTMS) [MH$^+$] C$_{24}$H$_{26}$N$_5$O$_2$ 416.2081, found: 416.2099

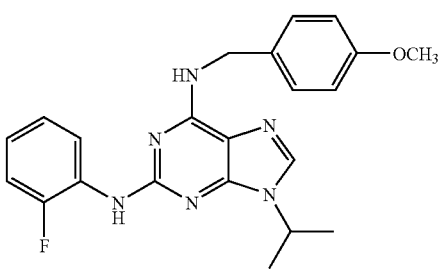

2-(2-fluorophenylamino)-6-(4-methoxybenzylamino)-9-isopropylpurine: $^1$H NMR (400 MHz, CDCl$_3$) δ 1.58 (d, 6H, J=6.8 Hz), 3.78 (s, 3H), 4.69 (m, 1H, J=6.8 Hz), 4.76 (br, 2H), 6.34 (br, 1H), 6.85 (d, 2H, J=8.4 Hz), 7.04–7.11(m, 2H), 7.14 (d, 1H, J=2.8 Hz), 7.30 (d, 2H, J=8.4 Hz), 7.50 (s, 1H), 8.62 (t, 1H, J=8.4 Hz); HRMS (MALDI-FTMS) [MH$^+$] C$_{22}$H$_{24}$FN$_6$O 407.1990, found: 407.1996.

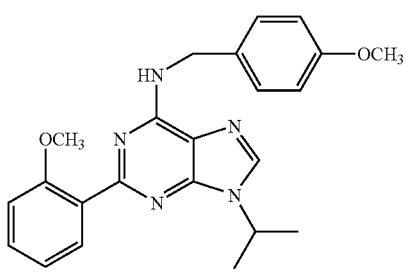

2-(2-methoxyphenyl)-6-(4-methoxybenzylamino)-9-isopropylpurine. $^1$H NMR (400 MHz, CDCl$_3$) δ 1.60 (d, 6H, J=6.8 Hz), 3.79 (s, 3H), 3.85 (s, 3H), 4.87 (d, 2H), 4.92 (m, 1H, J=6.8 Hz), 5.99 (br, 1H), 6.86 (d, 2H, J=8.5 Hz), 7.01–7.06 (m, 2H), 7.35 (m, 3H), 7.72 (d, 1H, J=7.2 Hz), 7.79 (s, 1H); HRMS (MALDI-FTMS) [MH$^+$] C$_{23}$H$_{26}$N$_5$O$_2$ 404.2081, found: 404.2056

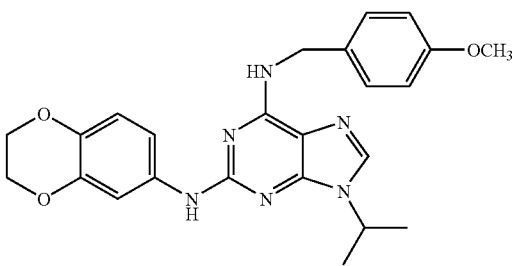

2-(1,4-benzodioxan-6-amino)-6-(4-methoxybenzylamino)-9-isopropylpurine: $^1$H NMR (400 MHz, CDCl$_3$) δ 1.56 (d, 6H, J=6.8 Hz), 3.78 (s, 3H), 4.24 (m, 4H), 4.70 (m, 1H, J=6.8 Hz), 4.72 (br, 2H), 6.14 (br, 1H), 6.77 (d, 1H, J=8.7 Hz), 6.85 (m, 3H), 6.99 (m, 1H), 7.29 (d, 2H, J=8.5 Hz), 7.44 (d, 1H, J=2.3 Hz), 7.49 (s, 1H); HRMS (MALDI-FTMS) [MH$^+$] C$_{24}$H$_{27}$N$_6$O$_3$ 447.2139, found: 447.2134

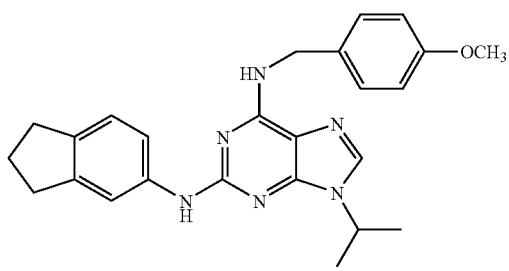

2-(indan-5-amino)-6-(4-methoxybenzylamino)-9-isopropylpurine: $^1$H NMR (400 MHz, CDCl$_3$) δ 1.57 (d, 6H, J=6.8 Hz), 2.06 (m, 2H), 2.86 (m, 4H), 3.78 (s, 3H), 4.69 (m, 1H, J=6.8 Hz), 4.75 (br, 2H), 6.09 (br, 1H), 6.85 (d, 2H, J=8.5 Hz), 6.92 (s, 1H); 7.13 (d, 1H, J=8.1 Hz), 7.29 (d, 2H, J=8.5 Hz), 7.40 (d, 1H, J=8.0 Hz), 7.50 (s, 1H), 7.60 (s, 1H); HRMS (MALDI-FTMS) [MH$^+$] C$_{25}$H$_{29}$N$_6$O 429.2397, found: 429.2417

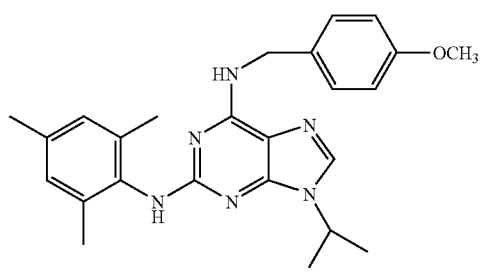

2-(2,4,6-tri-methylphenylamino)-6-(4-methoxybenzylamino)-9-isopropylpurine: $^1$H NMR (400 MHz, CDCl$_3$) δ 1.47 (d, 6H, J=6.8 Hz), 2.22 (s, 6H), 2.31 (s, 3H), 3.78 (s, 3H), 4.52 (br, 2H), 4.60 (m, 1H, J=6.8 Hz), 5.86 (br, 1H), 6.11 (br, 1H), 6.77 (d, 2H, J=8.4 Hz), 6.93 (s, 2H), 7.10 (d, 2H, J=7.5 Hz), 7.49 (s, 1H); HRMS (MALDI-FTMS) [MH$^+$] C$_{25}$H$_{31}$N$_6$O 431.2554, found: 431.2569

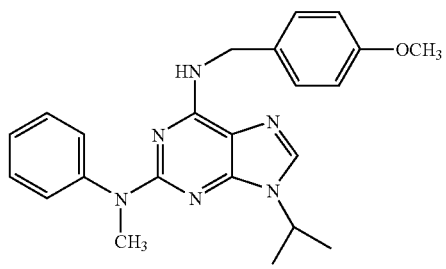

2-(N-methylphenylamino)-6-(4-methoxybenzylamino)-9-isopropylpurine: $^1$H NMR (400 MHz, CDCl$_3$) δ 1.52 (d, 6H, J=6.8 Hz), 3.57 (s, 3H), 3.77 (s, 3H), 4.54 (br, 2H), 4.62 (m, 1H, J=6.8 Hz), 5.92 (br, 1H), 6.79 (d, 2H, J=8.5 Hz), 7.10 (d, 1H, J=7.3 Hz), 7.15 (d, 2H, J=8.5 Hz), 7.32 (m, 2H), 7.38 (d, 2H, J=7.7 Hz), 7.48 (s, 1H); HRMS (MALDI-FTMS) [MH$^+$] C$_{23}$H$_{27}$N$_6$O 403.2241, found: 403.2249

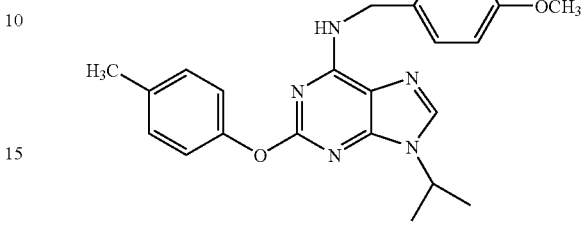

2-(4-methylphenoxy)-6-(4-methoxybenzylamino)-9-isopropylpurine. $^1$H NMR (400 MHz, CDCl$_3$) δ 1.53 (d, 6H, J=6.8 Hz), 2.37 (s, 3H), 3.79 (s, 3H), 4.54 (br, 2H), 4.71 (m, 1H, J=6.8 Hz), 6.35 (br, 1H), 6.81 (d, 2H, J=8.4 Hz), 7.10–7.18 (m, 6H), 7.65 (s, 1H); HRMS (MALDI-FTMS) [MH$^+$] C$_{23}$H$_{26}$N$_5$O$_2$ 404.2081, found: 404.2080

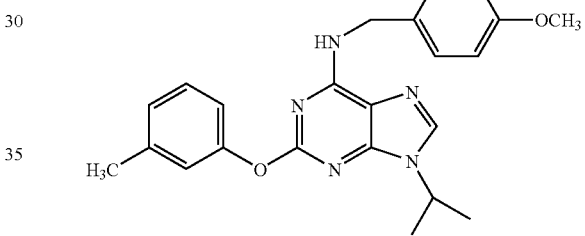

2-(3-methylphenoxy)-6-(4-methoxybenzylamino)-9-isopropylpurine. $^1$H NMR (400 MHz, CDCl$_3$) δ 1.53 (d, 6H, J=6.8 Hz), 2.37 (s, 3H), 3.78 (s, 3H), 4.52 (br, 2H), 4.71 (m, 1H, J=6.8 Hz), 6.62 (br, 1H), 6.81 (d, 2H, J=8.4 Hz), 7.00–7.05 (m, 3H), 7.14 (d, 2H, J=7.7 Hz), 7.25 (d, 1H, J=7.8 Hz), 7.66 (s, 1H); HRMS (MALDI-FTMS) [MH$^+$] C$_{23}$H$_{26}$N$_5$O$_2$ 404.2081, found: 404.2092

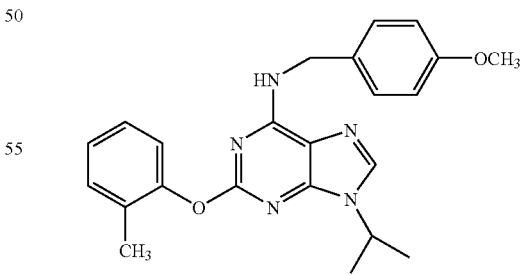

2-(2-methylphenoxy)-6-(4-methoxybenzylamino)-9-isopropylpurine. $^1$H NMR (400 MHz, CDCl$_3$) δ 1.52 (d, 6H, J=6.8 Hz), 2.20 (s, 3H), 3.78 (s, 3H), 4.42 (br, 2H), 4.71 (m, 1H, J=6.8 Hz), 6.63 (br, 1H), 6.77 (d, 2H, J=8.4 Hz), 7.04 (m, 2H), 7.11 (d, 1H, J=7.8 Hz), 7.15 (d, 1H, J=7.4 Hz), 7.21

(d, 1H, J=7.6 Hz), 7.25 (1H), 7.65 (s, 1H); HRMS (MALDI-FTMS) [MH$^+$] C$_{23}$H$_{26}$N$_5$O$_2$ 404.2081, found: 404.2087

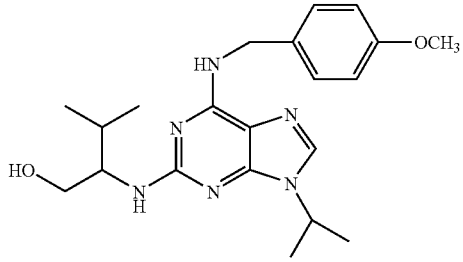

1H NMR (500 MHz, d6-DMSO) δ: d 0.85 (d, 6H, 7.1 Hz), 1.44 (d, 6H, 7.1 Hz), 1.93 (m, 1H), 3.31 (s, 2H), 3.46 (d, 2H, 5.3 Hz), 3.69 (s, 3H), 3.79 (m, 1H), 4.49 (m, 3H), 5.75 (s, 1H), 6.83 (d, 2H, J=8.7 Hz), 7.27 (d, 2H, J=8.7 Hz), 7.75 (s, 1H); HRMS calc'd for C$_{21}$H$_{30}$N$_6$O$_2$ [MH$^+$] 399.2508, found: 399.2510.

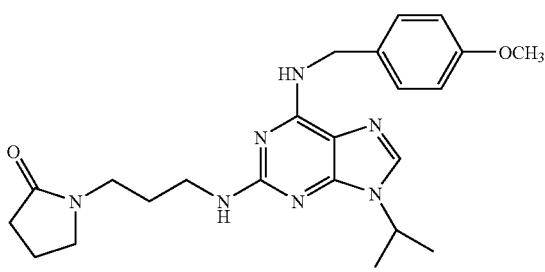

1H NMR (400 MHz, CDCl$_3$) δ: 1.61 (d, 6H, J=6.8 Hz), 1.92 (m, 2H), 2.10 (m, 2H), 2.52 (t, 2H, J=6.3 Hz), 3.44–3.56 (m, 6H), 3.80 (s, 3H), 4.81 (b, 3H)), 6.88 (d, 2H, J=7.9 Hz), 7.32 (d, 2H), 8.08 (s, 1H); MS (ES) calc'd for [MH$^+$] C$_{23}$H$_{32}$N$_7$O$_2$ 438.26, found 438.30

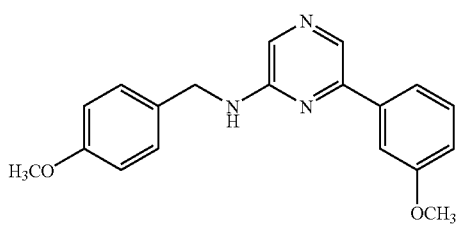

2-(4-methoxybenzylamino)-6-(3-methoxyphenyl)-pyrazine. $^1$H NMR (400 MHz, CDCl$_3$) δ 3.82 (s, 3H), 3.85 (s, 3H), 4.99 (br, 2H), 6.91–6.99 (m, 4H), 7.16 (d, 2H, J=8.8 Hz), 7.43–7.56 (m, 4H); MS (ES) calc'd for [MH$^+$] C$_{19}$H$_{20}$N$_3$O$_2$ 322.16, found 322.20

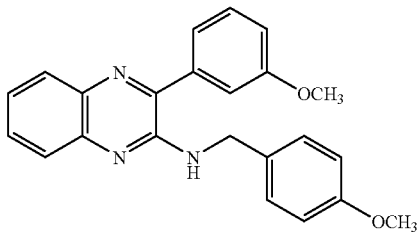

2-(4-methoxybenzylamino)-3-(3-methoxyphenyl)-quinoxaline. $^1$H NMR (400 MHz, CDCl$_3$) δ 3.79 (s, 3H), 3.84 (s, 3H), 4.95 (br, 2H), 5.86 (br, 1H), 6.87 (d, 2H, J=8.5 Hz), 7.05 (m, 1H), 7.25 (2H), 7.31 (d, 2H, J=8.4 Hz), 7.36 (m, 3H), 7.66 (m, 1H), 7.96 (d, 1H, J=8.1 Hz); MS (ES) calc'd for [MH$^+$] C$_{23}$H$_{22}$N$_3$O$_2$ 372.17, found 372.20

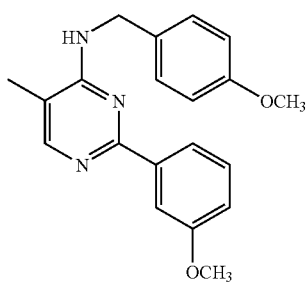

2-(3-methoxyphenyl)-4-(4-methoxybenzylamino)-5-methyl-quinoxaline. $^1$H NMR (400 MHz, CDCl$_3$) δ 2.15 (s, 3H), 3.89 (s, 3H), 3.98 (s, 3H), 4.87 (d 2H, J=5.4 Hz), 5.83 (br, 1H), 6.93 (d, 2H, J=8.6 Hz), 7.15 (dd, 1H), 7.33 (d, 2H, J=8.6 Hz), 7.45 (t, 1H, J=8.0 Hz), 8.14 (2H), 8.20 (d, 1H, J=8.3 Hz); MS (ES) calc'd for [MH$^+$] C$_{20}$H$_{22}$N$_3$O$_2$ 336.17, found 336.20

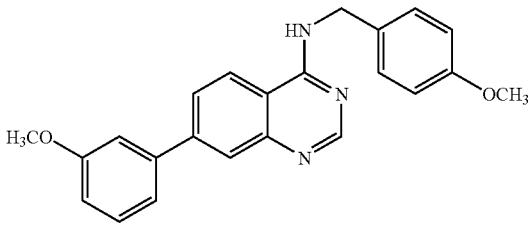

4-(4-methoxybenzylamino)-7-(3-methoxyphenyl)-quinazoline. $^1$H NMR (400 MHz, CDCl$_3$) δ 3.75 (s, 3H), 3.81 (s, 3H), 4.90 (br, 2H), 6.82 (m, 4H), 6.97 (2H), 7.47 (m, 4H), 8.21–8.49 (m, 3H); MS (ES) calc'd for [MH$^+$] C$_{23}$H$_{22}$N$_3$O$_2$ 372.17, found 372.20

It is understood that the examples and embodiments described herein are for illustrative purposes only and that various modifications or changes in light thereof will be suggested to persons skilled in the art and are to included within the spirit and purview of this application and are considered within the scope of the appended claims. All publications, patents, and patent applications cited herein are hereby incorporated by reference in their entirety for all purposes.

What is claimed is:

1. A method of preparing a C2-substituted purine compound, said method comprising:

reacting a C2-halogenated purine with a compound of Formula I

wherein X is a member selected from the group consisting of —B(OH)$_2$, —OH, and —NHR$^1$, wherein R$^1$ is a member selected from the group consisting of hydrogen, alkyl and substituted alkyl, and A is a member selected from the group consisting of alkyl, substituted alkyl, aryl, substituted aryl, heterocyclyl and substituted heterocyclyl;

in the presence of a solvent, a base, a carbene ligand and a palladium catalyst, to provide said C2-substituted purine compound.

2. The method of claim 1, wherein said C2-substituted purine compound has a Formula II

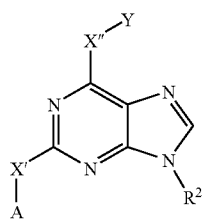

wherein R$^2$ is a member selected from the group consisting of hydrogen, alkyl, substituted alkyl, aryl, substituted aryl, heterocyclyl and substituted heterocyclyl;

X' is a member selected from the group consisting of a direct bond, NR$^1$ and O, wherein R$^1$ is as defined above;

X" is a member selected from the group consisting of a direct bond, O and NR$^3$;

Y is A';

A is as defined above;

A' is a member selected from the group consisting of alkyl, substituted alkyl, aryl, substituted aryl, arylalkyl, substituted arylalkyl, heterocyclyl and substituted heterocyclyl; and R$^3$ is a member selected from the group consisting of hydrogen, alkyl and substituted alkyl.

3. The method of claim 1, wherein said C2-halogenated purine has a Formula III

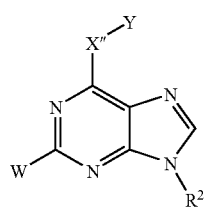

wherein W is a member selected from the group consisting of chloro, fluoro, bromo and iodo;

R$^2$ is a member selected from the group consisting of hydrogen, alkyl, substituted alkyl, aryl, substituted aryl, heterocyclyl and substituted heterocyclyl;

X" is a member selected from the group consisting of a direct bond, O and NR$^3$;

Y is A';

A' is a member selected from the group consisting of alkyl, substituted alkyl, aryl, substituted aryl, arylalkyl, substituted arylalkyl, heterocyclyl and substituted heterocyclyl; and R$^3$ is a member selected from the group consisting of hydrogen, alkyl and substituted alkyl.

4. The method of claim 1, wherein said carbene ligand is formed in situ from a precursor of the carbene ligand selected from the group consisting of

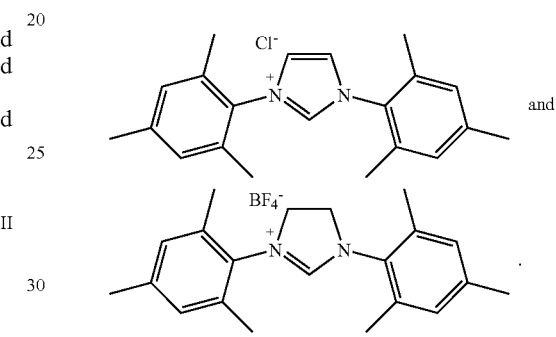

5. The method of claim 1, wherein X is —B(OH)$_2$ or NHR$^1$, and said solvent utilized in the reaction is 1,4-dioxane.

6. The method of claim 1, wherein X is —OH, and said solvent utilized in the reaction is toluene.

7. The method of claim 1, wherein the palladium catalyst is Pd$_2$(dibenzylideneacetone (dba))$_3$.

8. The method of claim 3, wherein in the compound of Formula III:

W is chloro;

R$^2$ is isopropyl;

X" is NR$^3$;

R$^3$ is hydrogen; and

A' is methoxybenzyl.

9. The method of claim 2, wherein X' is a direct bond and X is B(OH)$_2$.

10. The method of claim 1, wherein A is an aryl selected from the group consisting of phenyl, naphthyl and biphenyl, or is pyridinyl.

11. The method of claim 1, wherein A is a phenyl which is substituted with one or more substituents selected from the group consisting of lower alkyl, substituted lower alkyl, lower alkoxy, acyl and halo.

12. The method of claim 11, wherein said halo is fluoro.

13. The method of claim 9, wherein said base is Cs$_2$CO$_3$.

14. The method of claim 2, wherein X' is O and X is —OH.

15. The method of claim 14, wherein said base is potassium phosphate.

16. The method of claim 15, wherein said aryl is phenyl or naphthyl.

17. The method of claim 15, wherein said aryl is a phenyl substituted with one or more substituents selected from the group consisting of lower alkyl, wer alkoxy and halo.

18. The method of claim 2, wherein X' is $NR^1$ and X is $NHR^1$ wherein $R^1$ is as defined above.

19. The method of claim 18, wherein said base is potassium tert-butyloxide.

20. The method of claim 3, wherein in said compound of Formula III Y is A', wherein A' is a member selected from the group consisting of aryl, substituted aryl, heterocyclyl and substituted heterocyclyl.

* * * * *